United States Patent
Raptis et al.

(10) Patent No.: US 11,311,239 B2
(45) Date of Patent: Apr. 26, 2022

(54) SYSTEM AND METHOD FOR STORING AND FORWARDING DATA FROM A VITAL-SIGNS MONITOR

(71) Applicant: CareFusion 303, Inc., San Diego, CA (US)

(72) Inventors: Mark Raptis, Valley Center, CA (US); Amir Jafri, San Diego, CA (US); Ganesh Kathiresan, Osterley (GB); Alison Burdett, England (GB)

(73) Assignee: CAREFUSION 303, INC., San Diego, CA (US)

( * ) Notice: Subject to any disclaimer, the term of this patent is extended or adjusted under 35 U.S.C. 154(b) by 678 days.

(21) Appl. No.: 14/458,147

(22) Filed: Aug. 12, 2014

(65) Prior Publication Data
US 2014/0350362 A1 Nov. 27, 2014

Related U.S. Application Data

(63) Continuation of application No. 12/844,780, filed on Jul. 27, 2010, now Pat. No. 8,814,792.

(51) Int. Cl.
*A61B 5/00* (2006.01)
*A61B 5/01* (2006.01)
(Continued)

(52) U.S. Cl.
CPC .......... *A61B 5/6833* (2013.01); *A61B 5/0002* (2013.01); *A61B 5/002* (2013.01);
(Continued)

(58) Field of Classification Search
CPC ... A61B 5/0002; A61B 5/0015; A61B 5/0024; A61B 5/04; A61B 5/6801; H04W 56/00;
(Continued)

(56) References Cited

U.S. PATENT DOCUMENTS

| 3,677,261 A | 7/1972 | Day |
| 3,805,769 A | 4/1974 | Sessions |

(Continued)

FOREIGN PATENT DOCUMENTS

| EP | 1748289 A2 | 1/2007 |
| JP | 61003019 | 1/1986 |

(Continued)

OTHER PUBLICATIONS

Office Action dated May 3, 2012, which issued in U.S. Appl. No. 12/844,766.

(Continued)

*Primary Examiner* — Lori A. Clow
*Assistant Examiner* — Marie Archer
(74) *Attorney, Agent, or Firm* — Morgan, Lewis & Bockius LLP

(57) ABSTRACT

A vital-signs patch for a patient monitoring system that includes a housing containing a sensor that makes physiological measurements of a patient, a transmitter, a receiver, a memory, and a processor. The processor periodically takes a measurement from the sensor, converts the measurement to a data record, and stores the data record in the memory. Upon receipt of a signal from another device, the processor retrieves at least a portion of the data record, converts the retrieved portion of the data record to a vital-sign signal, and causes the transmitter to transmit the vital-sign signal to the other device.

20 Claims, 12 Drawing Sheets

(51) Int. Cl.

| | |
|---|---|
| *A61B 5/021* | (2006.01) |
| *A61B 5/024* | (2006.01) |
| *A61B 5/08* | (2006.01) |
| *H04L 1/18* | (2006.01) |
| *G16H 40/63* | (2018.01) |
| *G16H 10/60* | (2018.01) |
| *G16H 40/67* | (2018.01) |
| *G06F 13/16* | (2006.01) |
| *H04L 1/00* | (2006.01) |
| *H04W 56/00* | (2009.01) |
| *H04W 72/04* | (2009.01) |
| *H04L 67/125* | (2022.01) |

(52) U.S. Cl.
CPC .......... *A61B 5/0015* (2013.01); *A61B 5/0024* (2013.01); *A61B 5/01* (2013.01); *A61B 5/021* (2013.01); *A61B 5/024* (2013.01); *A61B 5/0816* (2013.01); *A61B 5/6801* (2013.01); *A61B 5/746* (2013.01); *G06F 13/1668* (2013.01); *G06F 13/1673* (2013.01); *G16H 10/60* (2018.01); *G16H 40/63* (2018.01); *G16H 40/67* (2018.01); *H04L 1/009* (2013.01); *H04L 1/0078* (2013.01); *H04L 1/0083* (2013.01); *H04L 1/0091* (2013.01); *H04L 1/1803* (2013.01); *H04L 1/1874* (2013.01); *H04L 67/125* (2013.01); *H04W 56/00* (2013.01); *H04W 72/0406* (2013.01); *H04W 72/0433* (2013.01); *Y10S 370/911* (2013.01); *Y10S 370/912* (2013.01); *Y10S 370/913* (2013.01)

(58) Field of Classification Search
CPC .......... H04W 72/0406; H04W 72/0433; H04L 1/0083; G06F 13/14; G06F 19/3406; G06F 19/3418
See application file for complete search history.

(56) References Cited

U.S. PATENT DOCUMENTS

| | | |
|---|---|---|
| 3,830,224 A | 8/1974 | Vanzetti et al. |
| 3,845,757 A | 11/1974 | Weyer |
| 4,121,574 A | 10/1978 | Lester |
| 4,396,020 A | 8/1983 | Wolff et al. |
| 4,407,295 A | 10/1983 | Steuer et al. |
| 4,490,005 A | 12/1984 | Hovey |
| 4,527,087 A | 7/1985 | Taya et al. |
| 4,530,366 A | 7/1985 | Nessi et al. |
| 4,539,996 A | 9/1985 | Engel |
| 4,541,734 A | 9/1985 | Ishizaka |
| 4,554,924 A | 11/1985 | Engel |
| 4,589,420 A * | 5/1986 | Adams ............... A61B 5/04525 600/515 |
| 4,640,289 A | 2/1987 | Craighead |
| 4,686,998 A | 8/1987 | Robbins |
| 4,708,146 A | 11/1987 | Lane |
| 4,715,382 A | 12/1987 | Strand |
| 4,765,340 A | 8/1988 | Sakai et al. |
| 4,771,713 A | 9/1988 | Kinzenbaw |
| 4,838,273 A | 6/1989 | Cartmell |
| 4,846,185 A | 7/1989 | Carim |
| 4,848,353 A | 7/1989 | Engel |
| 4,967,765 A | 11/1990 | Turner et al. |
| 5,012,810 A | 5/1991 | Strand et al. |
| 5,050,612 A | 9/1991 | Matsumura |
| 5,094,545 A | 3/1992 | Larsson et al. |
| 5,133,356 A | 7/1992 | Bryan et al. |
| 5,153,584 A | 10/1992 | Engira |
| 5,215,087 A | 6/1993 | Anderson et al. |
| 5,258,577 A | 11/1993 | Clements |
| 5,273,036 A | 12/1993 | Kronberg et al. |
| 5,285,577 A | 2/1994 | Carney et al. |
| 5,344,335 A | 9/1994 | Scholz et al. |
| 5,353,793 A | 10/1994 | Bornn |
| 5,401,100 A | 3/1995 | Thackston et al. |
| 5,511,553 A | 4/1996 | Segalowitz |
| 5,544,661 A | 8/1996 | Davis et al. |
| 5,634,468 A | 6/1997 | Platt et al. |
| 5,803,915 A | 9/1998 | Kremenchugsky et al. |
| 5,971,930 A | 10/1999 | Elghazzawi |
| 5,980,467 A | 11/1999 | Henry |
| 6,030,342 A | 2/2000 | Amano et al. |
| 6,042,966 A | 3/2000 | Cheu |
| 6,090,050 A | 7/2000 | Constantinides |
| 6,222,456 B1 | 4/2001 | Tice |
| 6,270,252 B1 | 8/2001 | Siefert |
| 6,273,886 B1 | 8/2001 | Edwards et al. |
| 6,287,252 B1 | 9/2001 | Lugo |
| 6,324,426 B1 | 11/2001 | Thompson |
| 6,355,031 B1 | 3/2002 | Edwards et al. |
| 6,358,245 B1 | 3/2002 | Edwards et al. |
| 6,416,471 B1 | 7/2002 | Kumar et al. |
| 6,454,708 B1 | 9/2002 | Ferguson et al. |
| 6,468,261 B1 | 10/2002 | Small et al. |
| 6,472,612 B2 | 10/2002 | Fartash et al. |
| 6,472,614 B1 | 10/2002 | Dupont et al. |
| 6,494,829 B1 | 12/2002 | New, Jr. et al. |
| 6,665,802 B1 | 1/2003 | Ober |
| 6,517,497 B2 | 2/2003 | Rymut et al. |
| 6,636,754 B1 | 10/2003 | Baura et al. |
| 6,719,701 B2 * | 4/2004 | Lade ................... A61N 1/3622 600/481 |
| 6,740,049 B2 | 5/2004 | Wallach |
| 6,740,059 B2 | 5/2004 | Flaherty |
| 6,950,688 B2 | 9/2005 | Axelgaard et al. |
| 6,963,772 B2 | 11/2005 | Bloom et al. |
| 6,980,112 B2 | 12/2005 | Nee |
| 7,061,858 B1 | 6/2006 | Di Benedetto et al. |
| 7,052,472 B1 | 8/2006 | Miller et al. |
| 7,139,605 B2 * | 11/2006 | Gerasimov .......... A61B 5/0456 600/519 |
| 7,198,600 B2 | 4/2007 | Tamaki et al. |
| 7,319,895 B2 | 1/2008 | Klefstad-Sillonville et al. |
| 7,355,512 B1 | 4/2008 | Al-Ali |
| RE40,470 E | 8/2008 | Fitzpatrick et al. |
| 7,434,991 B2 | 10/2008 | Harr et al. |
| 7,447,526 B2 | 11/2008 | Kim et al. |
| 7,538,682 B2 | 5/2009 | Trost et al. |
| 7,542,437 B1 | 6/2009 | Redi et al. |
| 7,639,352 B2 | 12/2009 | Huber et al. |
| 7,639,652 B1 | 12/2009 | Amis et al. |
| 7,645,263 B2 | 1/2010 | Angel et al. |
| 7,668,588 B2 | 2/2010 | Kovacs |
| 7,924,150 B2 | 4/2011 | Baldus et al. |
| 7,959,574 B2 | 6/2011 | Bardy |
| 7,962,188 B2 | 6/2011 | Kiani et al. |
| 8,007,436 B2 | 8/2011 | Katayama |
| 8,200,320 B2 | 6/2012 | Kovacs |
| 8,226,572 B2 | 7/2012 | Keith et al. |
| 8,228,188 B2 | 7/2012 | Key et al. |
| 8,231,542 B2 | 7/2012 | Keith et al. |
| 8,496,597 B2 | 7/2013 | James et al. |
| 8,506,480 B2 | 8/2013 | Banet et al. |
| 8,721,562 B2 | 5/2014 | Abreu |
| 9,055,925 B2 | 6/2015 | Paquet |
| 9,724,016 B1 * | 8/2017 | Al-Ali ..................... A61B 5/08 |
| 2001/0027384 A1 | 10/2001 | Schulze |
| 2001/0047127 A1 | 11/2001 | New, Jr. et al. |
| 2002/0007676 A1 | 1/2002 | Ward et al. |
| 2002/0013538 A1 | 1/2002 | Teller |
| 2002/0045836 A1 | 4/2002 | Alkawwas |
| 2002/0099277 A1 | 7/2002 | Harry et al. |
| 2002/0107436 A1 | 8/2002 | Barton et al. |
| 2002/0109621 A1 | 8/2002 | Khair et al. |
| 2002/0198519 A1 | 12/2002 | Qin et al. |
| 2003/0004403 A1 | 1/2003 | Drinan et al. |
| 2003/0028672 A1 * | 2/2003 | Goldstein ............... H04L 29/06 709/246 |
| 2003/0040305 A1 | 2/2003 | Ng et al. |
| 2003/0069510 A1 | 4/2003 | Semler et al. |

(56) References Cited

U.S. PATENT DOCUMENTS

| | | |
|---|---|---|
| 2003/0191445 A1 | 10/2003 | Wallen et al. |
| 2003/0212319 A1 | 11/2003 | Magill |
| 2003/0212340 A1 | 11/2003 | Lussier et al. |
| 2003/0229809 A1 | 12/2003 | Wexler et al. |
| 2004/0015058 A1 | 1/2004 | Besson et al. |
| 2004/0030259 A1 | 2/2004 | Dae et al. |
| 2004/0062133 A1 | 4/2004 | Tsuji |
| 2004/0073132 A1 | 4/2004 | Maahs et al. |
| 2004/0116822 A1 | 6/2004 | Lindsey |
| 2004/0165646 A1 | 8/2004 | Shidemantle et al. |
| 2004/0215098 A1 | 10/2004 | Barton et al. |
| 2004/0220538 A1 | 11/2004 | Panopoulos |
| 2004/0236188 A1 | 11/2004 | Hutchinson et al. |
| 2005/0085706 A1 | 4/2005 | Perrault et al. |
| 2005/0101843 A1 | 5/2005 | Quinn et al. |
| 2005/0131288 A1 | 6/2005 | Turner et al. |
| 2005/0159653 A1 | 7/2005 | Lijima et al. |
| 2005/0195079 A1 | 9/2005 | Cohen |
| 2005/0228297 A1 | 10/2005 | Banet et al. |
| 2005/0228299 A1 | 10/2005 | Banet |
| 2005/0231350 A1 | 10/2005 | Littrell et al. |
| 2005/0245831 A1 | 11/2005 | Banet |
| 2005/0245839 A1 | 11/2005 | Stivoric et al. |
| 2005/0249263 A1 | 11/2005 | Yerlikaya et al. |
| 2005/0251128 A1 | 11/2005 | Amoah |
| 2005/0280531 A1 | 12/2005 | Fadem et al. |
| 2006/0009697 A1 | 1/2006 | Banet et al. |
| 2006/0031102 A1 | 2/2006 | Teller |
| 2006/0045165 A1 | 3/2006 | Chan et al. |
| 2006/0047987 A1 | 3/2006 | Prabhakaran et al. |
| 2006/0094971 A1 | 5/2006 | Drew |
| 2006/0098576 A1 | 5/2006 | Brownrigg et al. |
| 2006/0155183 A1 | 7/2006 | Kroecker et al. |
| 2006/0202816 A1 | 9/2006 | Crump et al. |
| 2006/0224349 A1 | 10/2006 | Butterfield |
| 2006/0276714 A1 | 12/2006 | Holt et al. |
| 2007/0032706 A1 | 2/2007 | Kamath et al. |
| 2007/0041424 A1 | 2/2007 | Lev et al. |
| 2007/0099678 A1 | 5/2007 | Kim et al. |
| 2007/0116089 A1 | 5/2007 | Bisch et al. |
| 2007/0123756 A1 | 5/2007 | Kitajima et al. |
| 2007/0129622 A1 | 6/2007 | Bourget et al. |
| 2007/0135866 A1 | 6/2007 | Baker et al. |
| 2007/0142715 A1 | 6/2007 | Banet et al. |
| 2007/0185660 A1 | 8/2007 | Anderson |
| 2007/0191728 A1 | 8/2007 | Shennib |
| 2007/0208233 A1 | 9/2007 | Kovacs |
| 2007/0219434 A1 | 9/2007 | Abreu |
| 2007/0225614 A1 | 9/2007 | Naghavi et al. |
| 2007/0293781 A1 | 12/2007 | Sims et al. |
| 2008/0042866 A1 | 2/2008 | Morse et al. |
| 2008/0091090 A1 | 4/2008 | Guillory et al. |
| 2008/0097178 A1 | 4/2008 | Banet et al. |
| 2008/0097422 A1 | 4/2008 | Edwards et al. |
| 2008/0114220 A1 | 5/2008 | Banet et al. |
| 2008/0119707 A1 | 5/2008 | Stafford |
| 2008/0143512 A1 | 6/2008 | Wakisaka et al. |
| 2008/0183054 A1 | 7/2008 | Kroeger et al. |
| 2008/0200770 A1 | 8/2008 | Hubinette |
| 2008/0200774 A1 | 8/2008 | Luo |
| 2008/0208026 A1 | 8/2008 | Noujaim et al. |
| 2008/0214949 A1 | 9/2008 | Stivoric et al. |
| 2008/0221399 A1 | 9/2008 | Zhou et al. |
| 2008/0234600 A1 | 9/2008 | Marsh |
| 2008/0275327 A1 | 11/2008 | Faarbaek et al. |
| 2008/0294058 A1 | 11/2008 | Shklarski |
| 2008/0294065 A1 | 11/2008 | Waldhoff et al. |
| 2008/0305154 A1 | 12/2008 | Yanaki |
| 2009/0018409 A1 | 1/2009 | Banet et al. |
| 2009/0054737 A1 | 2/2009 | Magar et al. |
| 2009/0062670 A1 | 3/2009 | Sterling et al. |
| 2009/0069642 A1 | 3/2009 | Gao et al. |
| 2009/0073991 A1 | 3/2009 | Landrum |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076405 A1 | 3/2009 | Amurthur et al. |
| 2009/0076559 A1 | 3/2009 | Libbus et al. |
| 2009/0105549 A1 | 4/2009 | Smith et al. |
| 2009/0105605 A1 | 4/2009 | Abreu |
| 2009/0131759 A1 | 5/2009 | Sims et al. |
| 2009/0131774 A1 | 5/2009 | Sweitzer et al. |
| 2009/0182204 A1 | 7/2009 | Semler et al. |
| 2009/0203974 A1 | 8/2009 | Hickle |
| 2009/0209896 A1 | 8/2009 | Selevan |
| 2009/0227877 A1 | 9/2009 | Tran |
| 2009/0259139 A1 | 10/2009 | Stapien et al. |
| 2009/0270744 A1 | 10/2009 | Prstojevich et al. |
| 2009/0271681 A1 | 10/2009 | Piret et al. |
| 2009/0306536 A1 | 12/2009 | Ranganathan et al. |
| 2010/0010319 A1 | 1/2010 | Tivig et al. |
| 2010/0036212 A1 | 2/2010 | Rieth |
| 2010/0056886 A1 | 3/2010 | Hurtubise et al. |
| 2010/0056945 A1 | 3/2010 | Holmes |
| 2010/0056946 A1 | 3/2010 | Holmes |
| 2010/0056947 A1 | 3/2010 | Holmes |
| 2010/0081949 A1 | 4/2010 | Derby, Jr. |
| 2010/0100004 A1 | 4/2010 | van Someren |
| 2010/0113894 A1 | 5/2010 | Padiy |
| 2010/0121217 A1 | 5/2010 | Padiy et al. |
| 2010/0160745 A1 | 6/2010 | Hills et al. |
| 2010/0222688 A1 | 9/2010 | Fischell et al. |
| 2010/0234716 A1 | 9/2010 | Engel |
| 2010/0249541 A1* | 9/2010 | Geva .................. G06F 19/3418 600/301 |
| 2010/0249625 A1* | 9/2010 | Lin ...................... A61B 5/0002 600/515 |
| 2010/0286607 A1 | 11/2010 | Saltzstein |
| 2010/0292605 A1 | 11/2010 | Grassl et al. |
| 2010/0298656 A1 | 11/2010 | McCombie et al. |
| 2010/0298895 A1 | 11/2010 | Ghaffari et al. |
| 2010/0323634 A1 | 12/2010 | Kimura |
| 2010/0324548 A1 | 12/2010 | Godara et al. |
| 2011/0004076 A1 | 1/2011 | Janna et al. |
| 2011/0060252 A1 | 3/2011 | Simonsen et al. |
| 2011/0066062 A1 | 3/2011 | Banet et al. |
| 2011/0077497 A1 | 3/2011 | Oster et al. |
| 2011/0144470 A1 | 6/2011 | Mazar et al. |
| 2011/0160601 A1 | 6/2011 | Wang et al. |
| 2011/0176465 A1 | 7/2011 | Panta et al. |
| 2011/0182213 A1 | 7/2011 | Forssell et al. |
| 2011/0224557 A1 | 9/2011 | Banet et al. |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029308 A1 | 2/2012 | Paquet |
| 2012/0029309 A1 | 2/2012 | Paquet |
| 2012/0029310 A1 | 2/2012 | Paquet et al. |
| 2012/0029311 A1 | 2/2012 | Raptis et al. |
| 2012/0029312 A1 | 2/2012 | Beaudry et al. |
| 2012/0029313 A1 | 2/2012 | Burdett et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0030547 A1 | 2/2012 | Raptis et al. |
| 2012/0108920 A1 | 5/2012 | Bly et al. |
| 2012/0165621 A1 | 6/2012 | Grayzel et al. |
| 2012/0238901 A1 | 9/2012 | Augustine |
| 2012/0310070 A1 | 12/2012 | Kumar et al. |
| 2015/0223706 A1 | 8/2015 | Raptis et al. |
| 2015/0272515 A1 | 10/2015 | Paquet et al. |

FOREIGN PATENT DOCUMENTS

| | | |
|---|---|---|
| JP | 2002-507131 | 3/2002 |
| JP | 2004-503266 | 2/2004 |
| JP | 2005-521453 | 7/2005 |

(56) References Cited

FOREIGN PATENT DOCUMENTS

| | | |
|---|---|---|
| JP | 2009-544065 | 12/2009 |
| KR | 20070097725 | 10/2007 |
| KR | 100949150 | 3/2010 |
| WO | WO1990/012606 | 11/1990 |

OTHER PUBLICATIONS

Office Action dated Oct. 5, 2011, which issued in U.S. Appl. No. 12/844,766.
Office Action dated Jul. 10, 2012, which issued in U.S. Appl. No. 12/844,769.
Office Action dated Sep. 28, 2011, which issued in U.S. Appl. No. 12/844,769.
Office Action dated Mar. 21, 2012, which issued in U.S. Appl. No. 12/844,774.
Office Action dated Oct. 16, 2014, which issued in U.S. Appl. No. 12/844,774.
Office Action dated Jun. 4, 2014, which issued in U.S. Appl. No. 12/844,774.
Office Action dated Sep. 27, 2011, which issued in U.S. Appl. No. 12/844,774.
Office Action dated Oct. 16, 2014, which issued in U.S. Appl. No. 12/844,775.
Office Action dated Oct. 28, 2013, which issued in U.S. Appl. No. 12/844,775.
Office Action dated May 27, 2014, which issued in U.S. Appl. No. 12/844,775.
Office Action dated Jun. 20, 2012, which issued in U.S. Appl. No. 12/844,775.
Office Action dated Nov. 13, 2014, which issued in U.S. Appl. No. 12/844,771.
Office Action dated Oct. 28, 2013, which issued in U.S. Appl. No. 12/844,771.
Office Action dated Jun. 13, 2014, which issued in U.S. Appl. No. 12/844,771.
Office Action dated Jun. 22, 2012, which issued in U.S. Appl. No. 12/844,771.
Office Action dated Jan. 2, 2014, which issued in U.S. Appl. No. 12/844,780.
Office Action dated Aug. 2, 2013, which issued in U.S. Appl. No. 12/844,780.
Office Action dated Jul. 11, 2013, which issued in U.S. Appl. No. 12/844,789.
Office Action dated Dec. 7, 2012, which issued in U.S. Appl. No. 12/844,789.
Office Action dated Dec. 3, 2014, which issued in U.S. Appl. No. 12/844,796.
Office Action dated Dec. 16, 2013, which issued in U.S. Appl. No. 12/844,796.
Office Action dated Jun. 30, 2014, which issued in U.S. Appl. No. 12/844,796.
Office Action dated Jul. 9, 2013, which issued in U.S. Appl. No. 12/844,796.
Office Action dated Sep. 14, 2012, which issued in U.S. Appl. No. 12/844,801.
Office Action dated Apr. 12, 2012, which issued in U.S. Appl. No. 12/844,801.
Office Action dated Dec. 19, 2012, which issued in U.S. Appl. No. 12/844,788.
Office Action dated Jul. 16, 2012, which issued in U.S. Appl. No. 12/844,794.
Office Action dated Nov. 23, 2011, which issued in U.S. Appl. No. 12/844,794.
Office Action dated Dec. 21, 2012; which issued in U.S. Appl. No. 12/844,781.
Office Action dated Jul. 19, 2012, which issued in U.S. Appl. No. 12/844,765.
Office Action dated Nov. 18, 2011, which issued in U.S. Appl. No. 12/844,765.
Office Actions issued in U.S. Appl. No. 12/844,801, dated Aug. 14, 2014, and U.S. Appl. No. 12/844,794, dated Sep. 26, 2014.
W. J. Tompkins, Biomedical Digital Signal Processing. Prentice Hall, New Jersey, 1993; p. 1-378 (Year:1993).
Akyldiz, I.F. et al.; "Wireless Multimedia Sensor Networks: A survey." IEEE Wireless Communications. Dec. 2007, p. 32-39.
Arisha, K. et al. "System-Level Power Optimization for wireless Multimedia Communication." Editors: Ramesh K. and Goodman, D.; Springer US; 2002, p. 21-40.
Cardei, M. et al.; "Improving Wireless Sensor Network Lifetime through Power Aware Organization"; Wireless Networks 11, 222-240. 2005.
Davidson, K. G. et al., "Measurement of tidal volume by using transthoracic impedance variations in rats," J. Appl. Physiol. 86:759-766, 1999.
Ernst. J.M. et al, "Impedance Penumography: noise as signal in impedance cardiography," Psychophysiology, 36 (1999) 333-338.
Freundlich J.J. et al., Electrical Impedence Pneumography for Simple Nonrestrictive Continuous Monitoring of Respiratory Rate, Rhythm and Tidal Volume for Surgical Patients, Chest, 65, p. 181-184, 1974.
Herman, T. et al.; "A Distributed TDMA Slot Assignment Algorithm for Wireless Sensor Networks"; S. Nikoletseas and J. Rolim (Eds.): Algosensors 2004, LNCS 3121, pp. 45-58, 2004, Springer-Verlag Berlin Heidelberg 2004.
Hohlt, B. et al. "Flexible Power Scheduling for Sensor Networks," IPSN'04, Apr. 26-27, 2004, Berkeley, California, USA. p. 1-10.
Kelkar, S. P. et al., "Development of Movement artifact free breathing monitor," J. Instrum. Soc. India 38(1) 34-43, 2008.
Lee, W. L.; "Flexible-Schedule-Based TDMA Protocol for Fault-Tolerant and Energy-Efficient Wireless Sensor Networks," IEEE Transactions on Parallel and Distributed Systems, vol. 19, No. 6, Jun. 2008; p. 851-864.
Lee, W. L.; "Flexible-Schedule-Based TDMA Protocols for Supporting Fault-Tolerance, On-Demand TDMA Slot Transfer, and Peer-to-Peer Communication in Wireless Sensor Networks;" Thesis for the degree of Doctor in Philosophy, University of Western Australia, 2007, p. 1-213.
Loriga, G., et al., "Textile sensing interfaces for cardiopulmonary signs monitoring," Proceedings of the 2005 IEEE Engineering in Medicine and Biology 27th Annual Conference Shanghai, China, Sep. 1-4, 2005, p. 7349-7352.
Luo, S. et al., "The electrode system in Impedence-Based Ventilation Measurement," IEEE Transactions of biomedical Engineering, vol. 39, No. 11, Nov. 1992, p. 1130-1140.
Matthews, R., et al., "A Wearable Physiological Sensor Suite for Unobtrusive Monitoring of Physiological and Cognitive State," Proceedings of the 29th Annual International Conference of the IEEE EMBS Cite Internationale, Lyon, France, Aug. 23-26, 2007, pp. 1-6.
Pacela, A.F. "Impedance Pneumograph, a survey of instrumentation techniques," Med. & Biol. Engineering, vol. 4, p. 1-5, 1966.
Pantazis, N.A. et al.; "Energy efficiency in wireless sensor networks using sleep mode TDMA scheduling," Ad Hoc Networks 7 (2009) 322-343.
Paradiso, R. et al., "Awearable health care system based on knitted integrated sensors," IEEE transactions on Information Technology in biomedicine, vol. 9, No. 3, Sep. 2005, p. 337-344.
Park, et al., "Development of Flexible Self Adhesive Patch for Professional Heat Stress Monitoring Service," Proceedings of the 2005 IEEE Engineering in Medicine and Biology 27th Annual Conference Shanghai, China, Sep. 1-4, 2005, pp. 3789-3792.
Rashid, R. A. et al; "Development of Energy Aware TDMA-Based MAC Protocol for Wireless Sensor Network System," European Journal of Scientific, vol. 30 No. 4 (2009), pp. 571-578.
Shaw, G.A. et al., "Warfighter Physiological and Environmental Monitoring: A Study for the U.S. Army Research Institute in Environmental Medicine and the Soldier Systems Center," 2004, Lincoln Laboratory, MIT, pp. 1-141.
Zheng, W. W. et al. "Adaptive-frame-based Dynamic Slot Assignment Protocol for Tactical Data Link System," 2009 International

(56) References Cited

OTHER PUBLICATIONS

Conference of Networks Security, Wireless Communications and Trusted Computing, IEEE, p. 709-714.
Brown, B.H. et al., "Bipolar and Tetrapolar transfer impedence measurements from volume conductor," Electronics Letters, vol. 35, No. 25, 2000, pp. 2060-2062.
Cooley, W.L. et al., "A new design for an impedence pneumograph," Journal of Applied Physiology, vol. 25, No. 4, 1968, pp. 429-432.
Grenvik, A. et al., "Impedence Pneumography," Chest, vol. 62, No. 4, Oct. 1972, pp. 439-443.
Holt, T. et al., "Monitoring and recording of physiological data of the manned space flight program," Supplement to IEEE Transactions on Aerospace, Jun. 1965, p. 341-344.
Miller, Matthew J., et al., "On-Demand TDMA Scheduling for Energy Conservation in Sensor Networks," Technical Report, Jun. 2004, p. 1-10.
Murat, B., "Electrical Impedence Plethysmography," Wiley Encyclopedia of Biomedical Engineering, 2006, p. 1-10.
NPL_VitalSense_2006, p. 1-2.
Poon, C. S. et al., "Evaluation of two noninvasive techniques for exercise ventilatory measurements," IEEE Engineering in Medicine and Biology conference, 1988, pp. 0823-0824.
Shakian, A. V. et al., "Electrode Motion Artifacts in Electrical Impedence Pneumography," IEEE Transactions in Biomedical Engineering, vol. BME-32, No. 6, Jun. 1985, pp. 448-451.
Kessler, "TCP/IP and tcpdump Pocket reference Guide", Champlain College, 2006.
Zhihui Chen; Kohkhar, A. "Self organization and energy efficient TDMA MAC protocol by wake up for wireless sensor networks," Sensor and Ad Hoc Communications and Networks, 2004. IEEE SECON 2004. 2004 First Annual IEEE Communications Society Conference on, pp. 335-341. Oct. 2004.
International Search Report and Written Opinion in International Application No. PCT/US2011/045361, dated Apr. 6, 2012, 8 pages.
International Preliminary Report on Patentability in International Application No. PCT/US2011/045361, dated Jan. 29, 2013, 6 pages.
International Search Report and Written Opinion in International Application No. PCT/US2011/045258, dated Apr. 6, 2012, 12 pages.
International Preliminary Report on Patentability in International Application No. PCT/US2011/045258, dated Jan. 29, 2013, 5 pages.
International Search Report and Written Opinion in International Application No. PCT/US2011/045337, dated Feb. 9, 2012, 7 pages.
International Preliminary Report on Patentability in International Application No. PCT/US2011/045337, dated Jan. 9, 2013, 4 pages.
International Search Report and Written Opinion for International Application No. PCT/US2011/045408, dated Feb. 24, 2012, 6 pages.
International Preliminary Report on Patentability in International Application No. PCT/US2011/045408, dated Jan. 29, 2013, 4 pages.
International Search Report and Written Opinion in International Application No. PCT/US2011/045415, dated Feb. 24, 2012, 7 pages.
International Preliminary Report on Patentability in International Application No. PCT/US2011/045415, dated Jan. 29, 2013, 4 pages.
International Search Report and Written Opinion in International Application No. PCT/US2011/045425, dated Apr. 6, 2012, 7 pages.
International Preliminary Report on Patentability in International Application No. PCT/US2011/045425, dated Jan. 29, 2013, 5 pages.
International Search Report and Written Opinion in International Application No. PCT/US2011/045414, dated Feb. 24, 2012, 9 pages.
International Preliminary Report on Patentability in International Application No. PCT/US2011/045414, dated Jan. 29, 2013, 6 pages.
International Search Report and Written Opinion in International Application No. PCT/US2011/045419, dated Apr. 6, 2012, 7 pages.
International Preliminary Report on Patentability in International Application No. PCT/US2011/045419, dated Jan. 29, 2013, 5 pages.
International Search Report and Written Opinion in International Application No. PCT/US2011/045240, dated Mar. 15, 2012, 8 pages.
International Preliminary Report on Patentability in International Application No. PCT/US2011/045240, dated Jan. 29, 2013, 6 pages.
International Search Report and Written Opinion in International Application No. PCT/US2011/045256, dated Feb. 9, 2012, 12 pages.
International Preliminary Report on Patentability in International Application No. PCT/US2011/045256, dated Jan. 29, 2013, 4 pages.
International Search Report and Written Opinion in International Application No. PCT/US2011/045245, dated Mar. 28, 2012, 7 pages.
International Preliminary Report on Patentability in International Application No. PCT/US2011/045245, dated Jan. 29, 2013, 5 pages.
International Search Report and Written Opinion in International Application No. PCT/US2011/030088, dated Oct. 31, 2011, 7 pages.
International Preliminary Report on Patentability in International Application No. PCT/US2011/030088, dated Oct. 27, 2012, 13 pages.
International Search Report and Written Opinion in International Application No. PCT/US2011/045249, dated Mar. 12, 2012, 6 pages.
International Preliminary Report on Patentability in International Application No. PCT/US2011/045249, dated Jan. 29, 2013, 4 pages.

* cited by examiner

SYSTEM AND METHOD FOR STORING AND FORWARDING DATA FROM A VITAL-SIGNS MONITOR

CROSS-REFERENCES TO RELATED APPLICATIONS

This application is a continuation of U.S. patent application Ser. No. 12/844,780, filed Jul. 27, 2010, entitled "System and Method for Storing and Forwarding Data from a Vital-Signs Monitor," now U.S. Pat. No. 8,814,792, the contents of which is hereby incorporated in its entirety for all purposes.

BACKGROUND

Field

The present disclosure generally relates to systems and methods of physiological monitoring, and, in particular, relates to monitoring of vital signs of patients in hospitals.

Description of the Related Art

Some of the most basic indicators of a person's health are those physiological measurements that reflect basic body functions and are commonly referred to as a person's "vital signs." The four measurements commonly considered to be vital signs consider oxygen saturation ($S_{O2}$) to be a "fifth vital sign" particularly for pediatric or geriatric cases. Some or all of these measurements may be performed routinely upon a patient when they arrive at a healthcare facility, whether it is a routine visit to their doctor or arrival at an Emergency Room (ER).

Vital signs are frequently taken by a nurse using basic tools including a thermometer to measure body temperature, a sphygmomanometer to measure blood pressure, and a watch to count the number of breaths or the number of heart beats in a defined period of time which is then converted to a "per minute" rate. If a patient's pulse is weak, it may not be possible to detect a pulse by hand and the nurse may use a stethoscope to amplify the sound of the patient's heart beat so that she can count the beats. Oxygen saturation of the blood is most easily measured with a pulse oximeter.

When a patient is admitted to a hospital, it is common for vital signs to be measured and recorded at regular intervals during the patient's stay to monitor their condition. A typical interval is 4 hours, which leads to the undesirable requirement for a nurse to awaken a patient in the middle of the night to take vital sign measurements.

When a patient is admitted to an ER, it is common for a nurse to do a "triage" assessment of the patient's condition that will determine how quickly the patient receives treatment. During busy times in an ER, a patient who does not appear to have a life-threatening injury may wait for hours until more serious cases have been treated. While the patient may be reassessed at intervals while awaiting treatment, the patient may not be under observation between these reassessments.

Measuring certain vital signs is normally intrusive at best and difficult to do on a continuous basis. Measurement of body temperature, for example, is commonly done by placing an oral thermometer under the tongue or placing an infrared thermometer in the ear canal such that the tympanic membrane, which shared blood circulation with the brain, is in the sensor's field of view. Another method of taking a body temperature is by placing a thermometer under the arm, referred to as an "axillary" measurement as axilla is the Latin word for armpit. Skin temperature can be measured using a stick-on strip that may contain panels that change color to indicate the temperature of the skin below the strip.

Measurement of respiration is easy for a nurse to do, but relatively complicated for equipment to achieve. A method of automatically measuring respiration is to encircle the upper torso with a flexible band that can detect the physical expansion of the rib cage when a patient inhales. An alternate technique is to measure a high-frequency electrical impedance between two electrodes placed on the torso and detect the change in impedance created when the lungs fill with air. The electrodes are typically placed on opposite sides of one or both lungs, resulting in placement on the front and back or on the left and right sides of the torso, commonly done with adhesive electrodes connected by wires or by using a torso band with multiple electrodes in the strap.

Measurement of pulse is also relatively easy for a nurse to do and intrusive for equipment to achieve. A common automatic method of measuring a pulse is to use an electrocardiograph (ECG or EKG) to detect the electrical activity of the heart. An EKG machine may use 12 electrodes placed at defined points on the body to detect various signals associated with the heart function. Another common piece of equipment is simply called a "heart rate monitor." Widely sold for use in exercise and training, heart rate monitors commonly consist of a torso band, in which are embedded two electrodes held against the skin and a small electronics package. Such heart rate monitors can communicate wirelessly to other equipment such as a small device that is worn like a wristwatch and that can transfer data wirelessly to a PC.

Nurses are expected to provide complete care to an assigned number of patients. The workload of a typical nurse is increasing, driven by a combination of a continuing shortage of nurses, an increase in the number of formal procedures that must be followed, and an expectation of increased documentation. Replacing the manual measurement and logging of vital signs with a system that measures and records vital signs would enable a nurse to spend more time on other activities and avoid the potential for error that is inherent in any manual procedure.

SUMMARY

For some or all of the reasons listed above, there is a need for a hospital to be able to continuously monitor its patients in different settings within the hospital. In addition, it is desirable for this monitoring to be done with limited interference with a patient's mobility or interfering with their other activities.

Embodiments of the patient monitoring system disclosed herein measure certain vital signs of a patient, which include respiratory rate, pulse rate, and body temperature, on a regular basis and compare these measurements to preset limits.

In certain aspects of the present disclosure, a vital-signs patch is disclosed. The patch includes a housing containing at least one sensor configured to measure data pertaining to a physiology of a patient, a transmitter, a receiver, a memory, and a processor. The processor periodically takes a measurement from the sensor, converts the measurement to a data record, and stores the data record in the memory. Upon receipt of a signal from a second device via the receiver, the processor retrieves at least a portion of the data record, configures the retrieved portion of the data record into a vital-sign signal, and causes the transmitter to transmit the vital-sign signal to the other device.

In certain aspects of the present disclosure, a bridge is disclosed. The bridge includes first and second receivers, first and second transmitters, a memory, and a processor. The processor periodically causes the first transmitter to transmit a signal to a first device that will cause the first device to transmit a vital-sign signal, receives a vital-sign signal from the first device via the first transmitter, converts the vital sign signal to a data record, and stores the data record in the memory. Upon receipt of a signal from a second device via the second receiver, the processor retrieves at least a portion of the data record from the memory, configures the retrieved portion of the data record into a data signal, and causes the transmitter to transmit the data signal.

In one aspect of the present disclosure, a method of storing and forwarding vital sign data is disclosed. The method includes receiving at a second device vital-sign data from a first device, storing the vital-sign data, listening for a signal from a third device until the signal is received, retrieving at least a portion of the vital-sign data from storage, and transmitting the retrieved portion of the vital-sign data to the third device.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
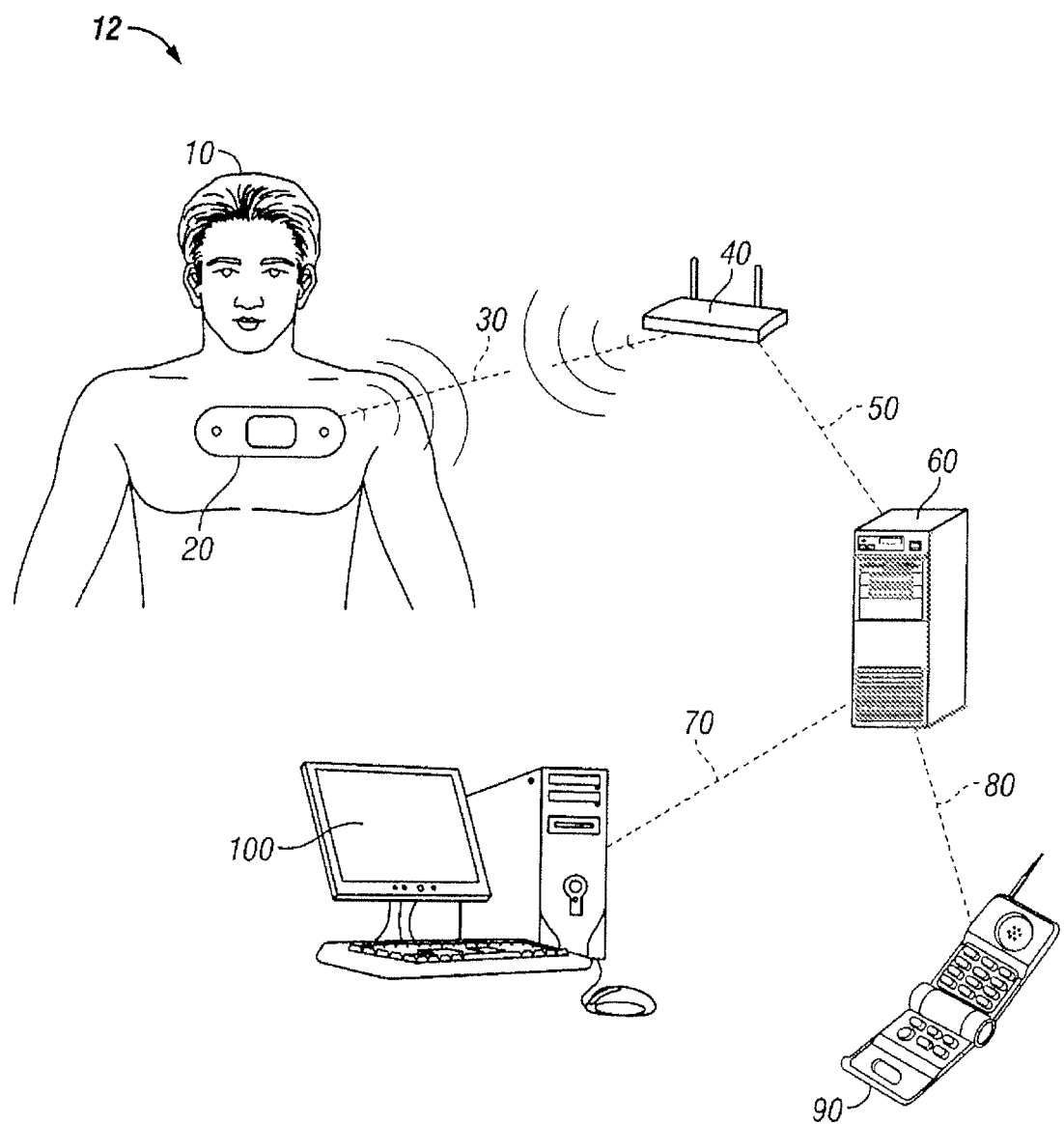
FIG. 1 is a diagram illustrating an exemplary embodiment of a patient monitoring system according to certain aspects of the present disclosure.

Periodic monitoring of patients in a hospital is desirable at least to ensure that patients do not suffer an un-noticed sudden deterioration in their condition or a secondary injury during their stay in the hospital. It is impractical to provide continuous monitoring by a clinician and cumbersome to connect sensors to a patient, which are then connected to a fixed monitoring instrument by wires. Furthermore, systems that sound an alarm when the measured value exceeds a threshold value may sound alarms so often and in situations that are not truly serious that such alarms are ignored by clinicians.

Measuring vital signs is difficult to do on a continuous basis. Accurate measurement of cardiac pulse, for example, can be done using an electrocardiograph (ECG or EKG) to detect the electrical activity of the heart. An EKG machine may use up to 12 electrodes placed at various points on the body to detect various signals associated with the cardiac function. Another common piece of equipment is termed a "heart rate monitor." Widely sold for use in exercise and physical training, heart rate monitors may comprise a torso band in which are embedded two electrodes held against the skin and a small electronics package. Such heart rate monitors can communicate wirelessly to other equipment such as a small device that is worn like a wristwatch and that can transfer data wirelessly to a personal computer (PC).

Monitoring of patients that is referred to as "continuous" is frequently periodic, in that measurements are taken at intervals. In many cases, the process to make a single measurement takes a certain amount of time, such that even back-to-back measurements produce values at an interval equal to the time that it takes to make the measurement. For the purpose of vital sign measurement, a sequence of repeated measurements can be considered to be "continuous" when the vital sign is not likely to change an amount that is of clinical significance within the interval between measurements. For example, a measurement of blood pressure every 10 minutes may be considered "continuous" if it is considered unlikely that a patient's blood pressure can change by a clinically significant amount within 10 minutes. The interval appropriate for measurements to be considered continuous may depend on a variety of factors including the type of injury or treatment and the patient's medical history. Compared to intervals of 4-8 hours for manual vital sign measurement in a hospital, measurement intervals of 30 minutes to several hours may still be considered "continuous."

Certain exemplary embodiments of the present disclosure include a system that comprises a vital-signs monitor patch that is attached to the patient, and a bridge that communicates with monitor patches and links them to a central server that processes the data, where the server can send data and alarms to a hospital system according to algorithms and protocols defined by the hospital.

The construction of the vital-signs monitor patch is described according to certain aspects of the present disclosure. As the patch may be worn continuously for a period of time that may be several days, as is described in the following disclosure, it is desirable to encapsulate the components of the patch such that the patient can bathe or shower and engage in their normal activities without degradation of the patch function. An exemplary configuration of the construction of the patch to provide a hermetically sealed enclosure about the electronics is disclosed.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail on as not to obscure the disclosure.

FIG. 1 discloses a vital sign monitoring system according to certain embodiments of the present disclosure. The vital sign monitoring system 12 includes vital-signs monitor patch 20, bridge 40, and surveillance server 60 that can send messages or interact with peripheral devices exemplified by mobile device 90 and workstation 100.

Monitor patch 20 resembles a large adhesive bandage and is applied to a patient 10 when in use. It is preferable to apply the monitor patch 20 to the upper chest of the patient 10 although other locations may be appropriate in some circumstances. Monitor patch 20 incorporates one or more electrodes (not shown) that are in contact with the skin of patient 10 to measure vital-signs such as cardiac pulse rate and respiration rate. Monitor patch 20 also may include other sensors such as an accelerometer, a temperature sensor, or an oxygen saturation sensor to measure other characteristics associated with the patient. These other sensors may be internal to the monitor patch 20 or external sensors that are operably connected to the monitor patch 20 via a cable or wireless connection. Monitor patch 20 also includes a wireless transmitter that can both transmit and receive signals. This transmitter is preferably a short-range, low-power radio frequency (RF) device operating in one of the unlicensed radio bands. One band in the United States (US) is, for example, centered at 915 MHz and designated for industrial, scientific and medical (ISM) purposes. An example of an equivalent band in the European Union (EU) is centered at 868 MHz. Other frequencies of operation may be possible dependent upon the International Telecommunication Union (ITU), local regulations and interference from other wireless devices.

Surveillance server 60 may be a standard computer server connected to the hospital communication network and preferably located in the hospital data center or computer room, although other locations may be employed. The server 60 stores and processes signals related to the operation of the patient monitoring system 12 disclosed herein including the association of individual monitor patches 20 with patients 10 and measurement signals received from multiple monitor patches 20. Hence, although only a single patient 10 and monitor patch 20 are depicted in FIG. 1, the server 60 is able to monitor the monitor patches 20 for multiple patients 10.

Bridge 40 is a device that connects, or "bridges", between monitor patch 20 and server 60. Bridge 40 communicates with monitor patch 20 over communication link 30 operating, in these exemplary embodiments, at approximately 915 MHz and at a power level that enables communication link 30 to function up to a distance of approximately 10 meters. It is preferable to place a bridge 40 in each room and at regular intervals along hallways of the healthcare facility where it is desired to provide the ability to communicate with monitor patches 20. Bridge 40 also is able to communicate with server 60 over network link 50 using any of a variety of computer communication systems including hardwired and wireless Ethernet using protocols such as 802.11a/b/g or 802.3af. As the communication protocols of communication link 30 and network link 50 may be very different, bridge 40 provides data buffering and protocol conversion to enable bidirectional signal transmission between monitor patch 20 and server 60.

While the embodiments illustrated by FIG. 1 employ a bridge 20 to provide communication link between the monitor patch 20 and the server 60, in certain alternative embodiments, the monitor patch 20 may engage in direct wireless communication with the server 60. In such alternative embodiments, the server 60 itself or a wireless modem connected to the server 60 may include a wireless communication system to receive data from the monitor patch 20.

In use, a monitor patch 20 is applied to a patient 10 by a clinician when it is desirable to continuously monitor basic vital signs of patient 10 while patient 10 is, in this embodiment, in a hospital. Monitor patch 20 is intended to remain attached to patient 10 for an extended period of time, for example, up to 5 days in certain embodiments, limited by the battery life of monitor patch 20. In some embodiments, monitor patch 20 is disposable when removed from patient 10.

Server 60 executes analytical protocols on the measurement data that it receives from monitor patch 20 and provides this information to clinicians through external workstations 100, preferably personal computers (PCs), laptops, or smart phones, over the hospital network 70. Server 60 may also send messages to mobile devices 90, such as cell phones or pagers, over a mobile device link 80 if a measurement signal exceeds specified parameters. Mobile device link 80 may include the hospital network 70 and internal or external wireless communication systems that are capable of sending messages that can be received by mobile devices 90.

Figure 2A:
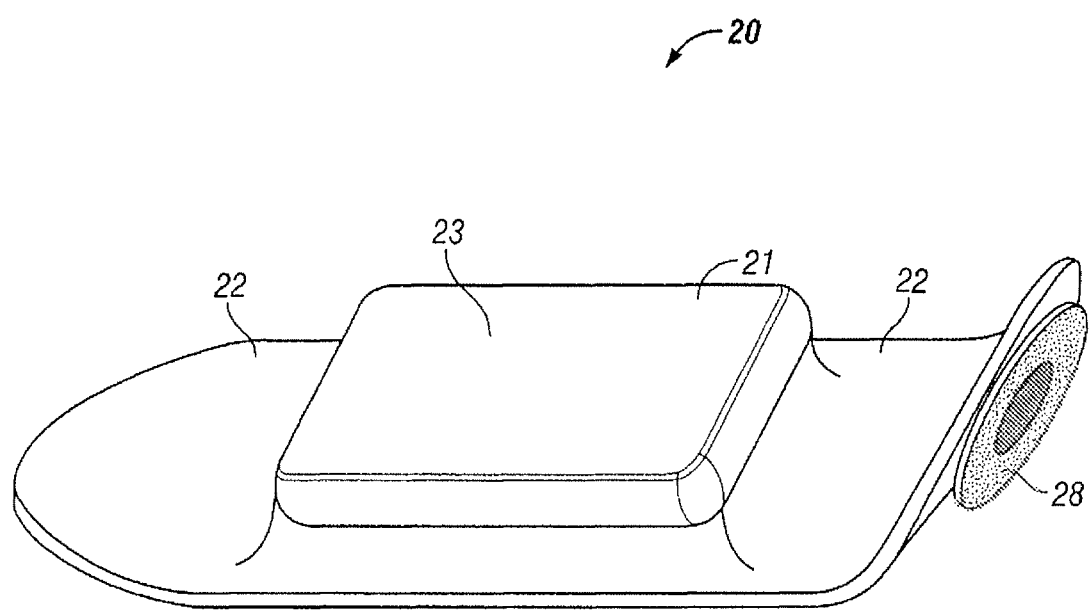
FIG. 2A is a perspective view of the vital-signs monitor patch of FIG. 1 according to certain aspects of the present disclosure.

FIG. 2A is a perspective view of the vital-signs monitor patch 20 shown in FIG. 1 according to certain aspects of the present disclosure. In the illustrated embodiment, the monitor patch 20 includes component carrier 23 comprising a central segment 21 and side segments 22 on opposing sides of the central segment 21. In certain embodiments, the central segment 21 is substantially rigid and includes a circuit assembly (24, FIG. 28) having electronic components and a battery mounted to a rigid printed circuit board (PCB). The side segments 22 are flexible and include a flexible conductive circuit (26, FIG. 28) that connect the circuit assembly 24 to electrodes 28 disposed at each end of the monitor patch 20, with side segment 22 on the right shown as being bent upwards for purposes of illustration to make one of the electrodes 28 visible in this view.

Figure 2B:
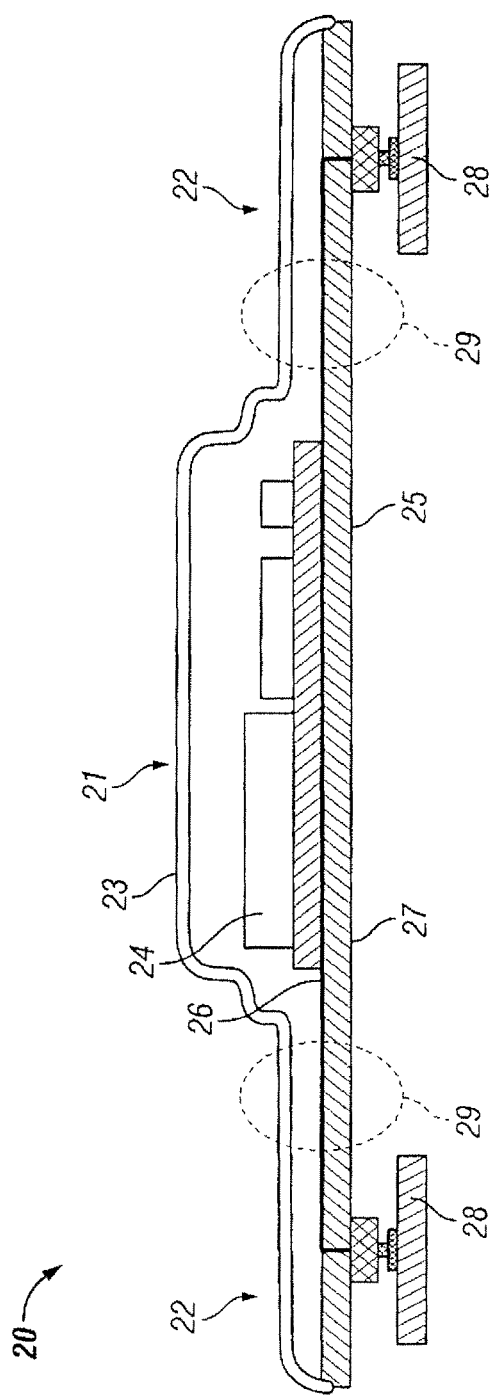
FIG. 2B is a cross-section of the vital-signs monitor patch of FIG. 1 according to certain aspects of the present disclosure.

FIG. 2B is a cross-sectional view of the vital-signs patch 20 shown in FIGS. 1 and 2A according to certain aspects of the present disclosure. The circuit assembly 24 and flexible conductive circuit 26 described above can be seen herein. The flexible conductive circuit 26 operably connects the circuit assembly 24 to the electrodes 28. Top and bottom layers 23 and 27 form a housing 25 that encapsulate circuit assembly 28 to provide a water and particulate barrier as well as mechanical protection. There are sealing areas on layers 23 and 27 that encircles circuit assembly 28 and is visible in the cross-section view of FIG. 2B as areas 29. Layers 23 and 27 are sealed to each other in this area to form a substantially hermetic seal. Within the context of certain aspects of the present disclosure, the term 'hermetic' implies that the rate of transmission of moisture through the seal is substantially the same as through the material of the layers that are sealed to each other, and further implies that the size of particulates that can pass through the seal are below the size that can have a significant effect on circuit assembly 24. Flexible conductive circuit 26 passes through portions of sealing areas 29 and the seal between layers 23 and 27 is maintained by sealing of layers 23 and 27 to flexible circuit assembly 28. The layers 23 and 27 are thin and flexible, as is the flexible conductive circuit 26, allowing the side segment 22 of the monitor patch 20 between the electrodes 28 and the circuit assembly 24 to bend as shown in FIG. 2A.

Figure 2C:
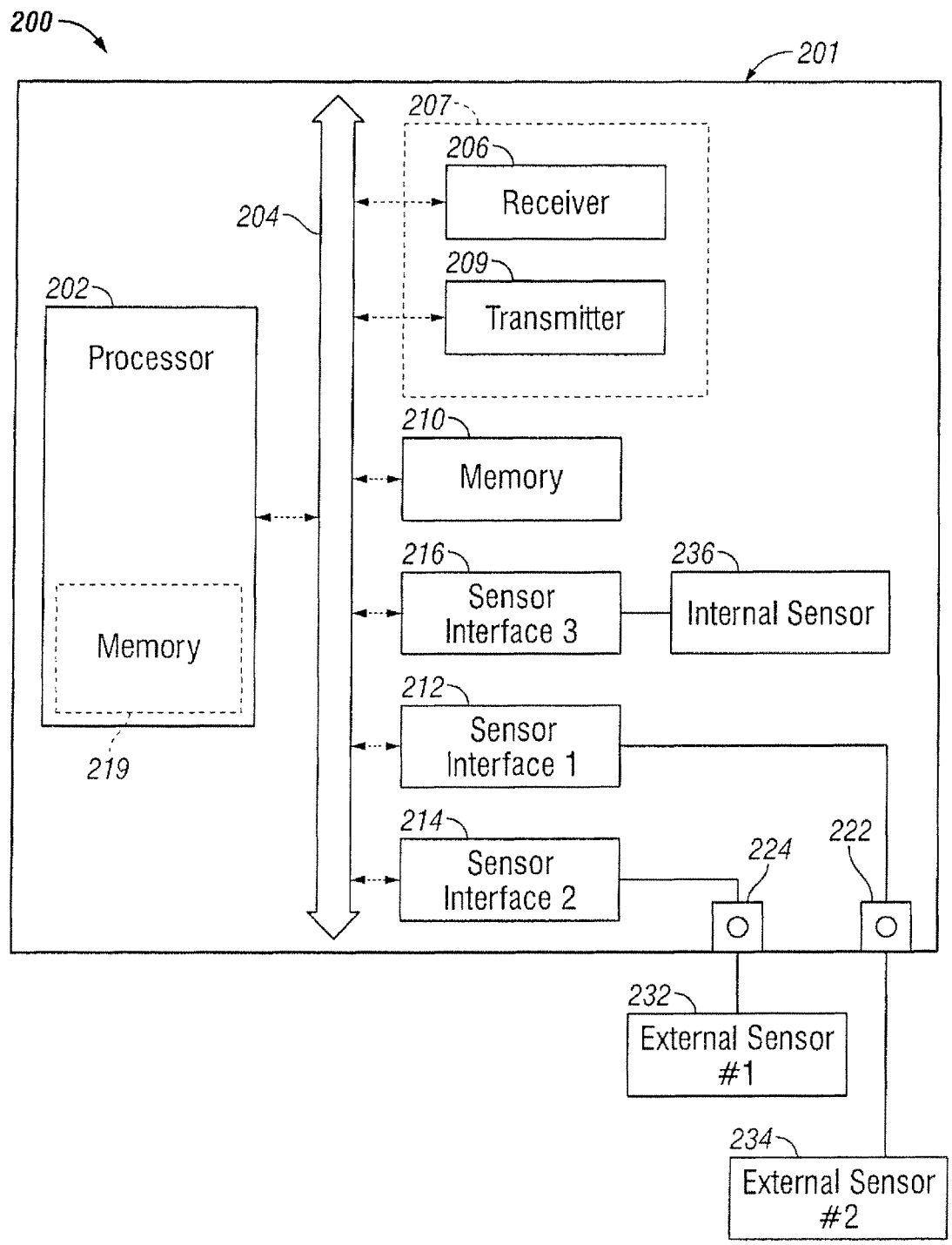
FIG. 2C is a functional block diagram illustrating exemplary electronic and sensor components of the vital-signs monitor patch of FIG. 1 according to certain aspects of the present disclosure.

FIG. 2C is a functional block diagram 200 illustrating exemplary electronic and sensor components of the monitor patch 20 of FIG. 1 according to certain aspects of the present disclosure. The block diagram 200 shows a processing and sensor interface module 201 and external sensors 232, 234 connected to the module 201. In the illustrated example, the module 201 includes a processor 202, a wireless transceiver 207 having a receiver 206 and a transmitter 209, a memory 210, a first sensor interface 212, a second sensor interface 214, a third sensor interface 216, and an internal sensor 236 connected to the third sensor interface 216. The first and second sensor interfaces 212 and 214 are connected to the first and second external sensors 232, 234 via first and second connection ports 222, 224, respectively. In certain embodiments, some or all of the aforementioned components of the module 201 and other components are mounted on a PCB.

Each of the sensor interfaces 212, 214, 216 can include one or more electronic components that are configured to generate an excitation signal or provide DC power for the sensor that the interface is connected to and/or to condition and digitize a sensor signal from the sensor. For example, the sensor interface can include a signal generator for generating an excitation signal or a voltage regulator for providing power to the sensor. The sensor interface can further include an amplifier for amplifying a sensor signal from the sensor and an analog-to-digital converter for digitizing the amplified sensor signal. The sensor interface can further include a filter (e.g., a low-pass or bandpass filter) for filtering out spurious noises (e.g., a 60 Hz noise pickup).

The processor 202 is configured to send and receive data (e.g., digitized signal or control data) to and from the sensor interfaces 212, 214, 216 via a bus 204, which can be one or more wire traces on the PCB. Although a bus communication topology is used in this embodiment, some or all communication between discrete components can also be implemented as direct links without departing from the scope of the present disclosure. For example, the processor 202 may send data representative of an excitation signal to the sensor excitation signal generator inside the sensor interface and receive data representative of the sensor signal from the sensor interface, over either a bus or direct data links between processor 202 and each of sensor interface 212, 214, and 216.

The processor 202 is also capable of communication with the receiver 206 and the transmitter 209 of the wireless transceiver 207 via the bus 204. For example, the processor 202 using the transmitter and receiver 209, 206 can transmit and receive data to and from the bridge 40. In certain embodiments, the transmitter 209 includes one or more of a RF signal generator (e.g., an oscillator), a modulator (a mixer), and a transmitting antenna; and the receiver 206 includes a demodulator (a mixer) and a receiving antenna which may or may not be the same as the transmitting antenna. In some embodiments, the transmitter 209 may include a digital-to-analog converter configured to receive data from the processor 202 and to generate a base signal; and/or the receiver 206 may include an analog-to-digital converter configured to digitize a demodulated base signal and output a stream of digitized data to the processor 202. In other embodiments, the radio may comprise a direct sequence radio, a software-defined radio, or an impulse spread spectrum radio.

The processor 202 may include a general-purpose processor or a specific-purpose processor for executing instructions and may further include a memory 219, such as a volatile or non-volatile memory, for storing data and/or instructions for software programs. The instructions, which may be stored in a memory 219 and/or 210, may be executed by the processor 202 to control and manage the wireless transceiver 207, the sensor interfaces 212, 214, 216, as well as to provide other communication and processing functions.

The processor 202 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information, such as program instructions, data representative of sensor readings, preset alarm conditions, threshold limits, may be stored in a computer or in a processor readable medium such as a memory internal to the processor 202 (e.g., the memory 219) or a memory external to the processor 202 (e.g., the memory 210), such as a Random Access Memory (RAM), a flash memory, a Read Only Memory (ROM), a Programmable Read-Only Memory (PROM), an Erasable PROM (EPROM), registers, a hard disk, a removable disk, or any other suitable storage device.

In certain embodiments, the internal sensor 236 can be one or more sensors configured to measure certain properties of the processing and sensor interface module 201, such as a board temperature sensor thermally coupled to a PCB. In other embodiments, the internal sensor 236 can be one or more sensors configured to measure certain properties of the patient 10, such as a motion sensor (e.g., an accelerometer) for measuring the patient's motion or position with respect to gravity.

The external sensors 232, 234 can include sensors and sensing arrangements that are configured to produce a signal representative of one or more vital signs of the patient to which the monitor patch 20 is attached. For example, the first external sensor 232 can be a set of sensing electrodes that are affixed to an exterior surface of the monitor patch 20 and configured to be in contact with the patient for measuring the patient's respiratory rate, and the second external sensor 234 can include a temperature sensing element (e.g., a thermocouple or a thermistor or resistive thermal device (RTD)) affixed, either directly or via an interposing layer, to skin of the patient 10 for measuring the patient's body temperature. In other embodiments, one or more of the external sensors 232, 234 or one or more additional external sensors can measure other vital signs of the patient, such as blood pressure, pulse rate, or oxygen saturation.

Figure 3A:
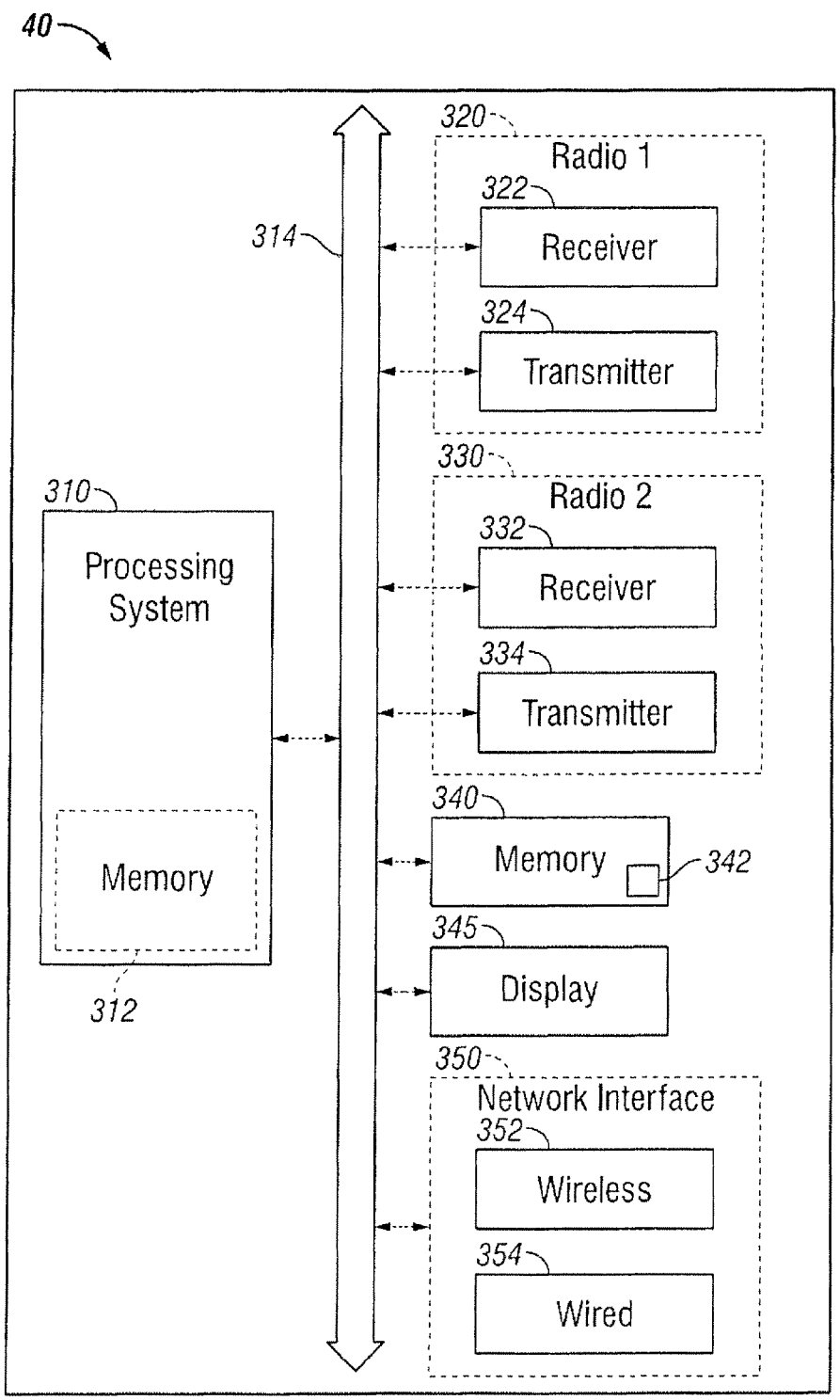
FIG. 3A is a functional schematic diagram of the bridge according to certain aspects of the subject disclosure.

FIG. 3A is a functional block diagram illustrating exemplary electronic components of bridge 40 of FIG. 1 according to one aspect of the subject disclosure. Bridge 40 includes a processor 310 310, radio 320 having a receiver 322 and a transmitter 324, radio 330 having a receiver 332 and a transmitter 334, memory 340, display 345, and network interface 350 having a wireless interface 352 and a wired interface 354. In some embodiments, some or all of the aforementioned components of module 300 may be integrated into single devices or mounted on PCBs.

Processor 310 is configured to send data to and receive data from receiver 322 and transmitter 324 of radio 320, receiver 332 and transmitter 334 of radio 330 and wireless interface 352 and wired interface 354 of network interface 350 via bus 314. In certain embodiments, transmitters 324 and 334 may include a radio frequency signal generator (oscillator), a modulator, and a transmitting antenna, and the receivers 322 and 332 may include a demodulator and antenna which may or may not be the same as the transmitting antenna of the radio. In some embodiments, transmitters 324 and 334 may include a digital-to-analog converter configured to convert data received from processor 310 and to generate a base signal, while receivers 322 and 332 may include analog-to-digital converters configured to convert a demodulated base signal and sent a digitized data stream to processor 310.

Processor 310 may include a general-purpose processor or a specific-purpose processor for executing instructions and may further include a memory 312, such as a volatile or non-volatile memory, for storing data and/or instructions for software programs. The instructions, which may be stored in memories 312 or 340, may be executed by the processor 310 to control and manage the transceivers 320, 330, and 350 as well as provide other communication and processing functions.

Processor 310 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 312 internal to processor 310 or in memory 340 external to processor 310 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 312 or 340 can also store a list or a database of established communication links and their corresponding characteristics (e.g., signal levels) between the bridge 40 and its related monitor patches 20. In the illustrated example of FIG. 3A, the memory 340 external to the processor 310 includes such a database 342; alternatively, the memory 312 internal to the processor 310 may include such a database.

Figure 3B:
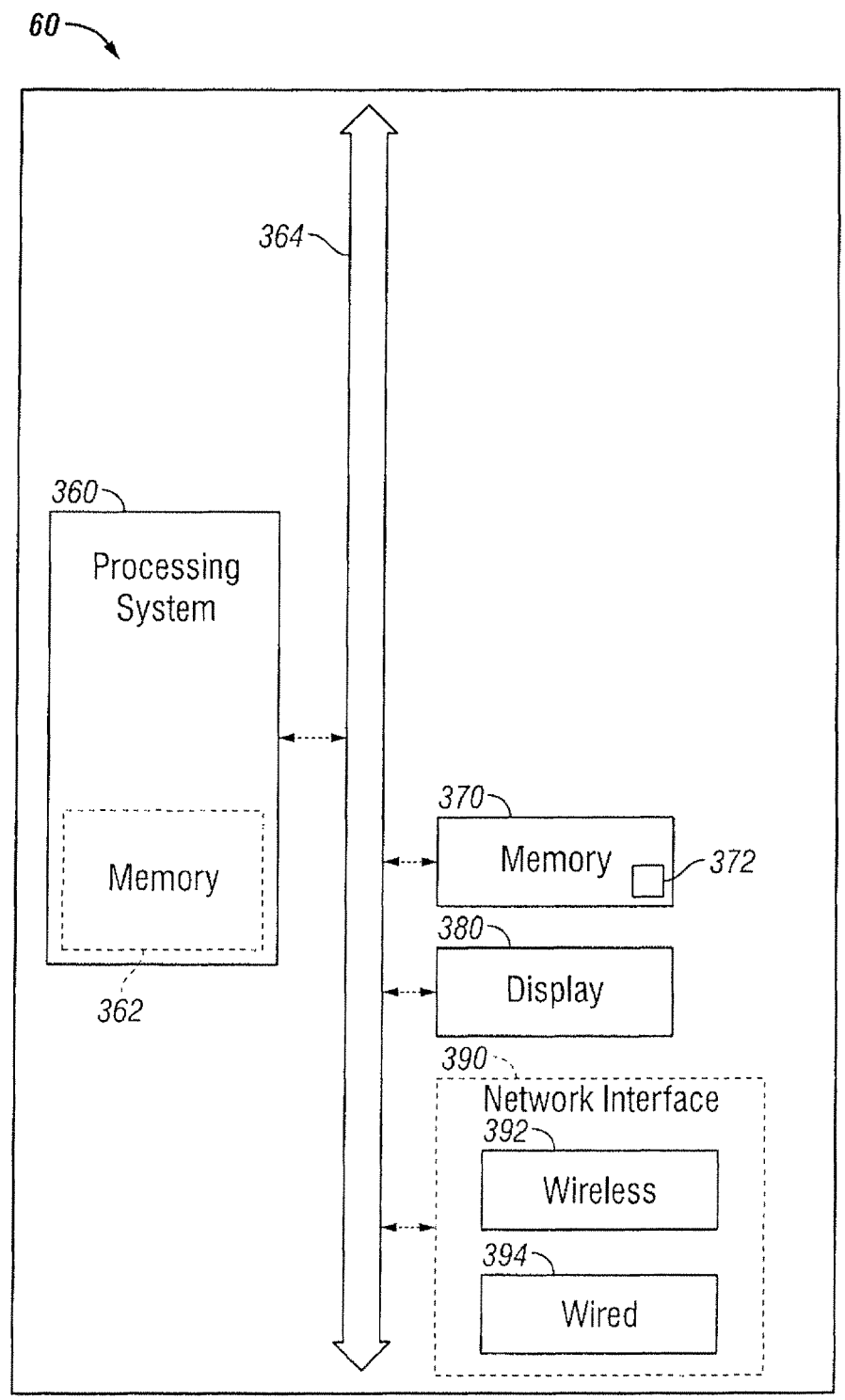
FIG. 3B is a functional schematic diagram of an embodiment of the surveillance server according to certain aspects of the present disclosure.

FIG. 3B is a functional block diagram illustrating exemplary electronic components of server 60 of FIG. 1 according to one aspect of the subject disclosure. Server 60 includes a processor 360, memory 370, display 380, and network interface 390 having a wireless interface 392 and a wired interface 394. Processor 360 may include a general-purpose processor or a specific-purpose processor for executing instructions and may further include a memory 362, such as a volatile or non-volatile memory, for storing data and/or instructions for software programs. The instructions, which may be stored in memories 362 or 370, may be executed by the processor 360 to control and manage the wireless and wired network interfaces 392, 394 as well as provide other communication and processing functions.

Processor 360 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device or a combination of devices that can perform calculations or other manipulations of information.

Information such as data representative of sensor readings may be stored in memory 362 internal to processor 360 or in memory 370 external to processor 360 which may be a Random Access Memory (RAM), flash memory, Read Only Memory (ROM), Programmable Read Only Memory (PROM), Erasable Programmable Read Only Memory (EPROM), registers, a hard disk, a removable disk, a Solid State Memory (SSD), or any other suitable storage device.

Memory 362 or 370 can also store a database of communication links and their corresponding characteristics (e.g., signal levels) between monitor patches 20 and bridges 40. In the illustrated example of FIG. 3B, the memory 370 external to the processor 360 includes such a database 372; alternatively, the memory 362 internal to the processor 360 may include such a database.

Figure 4:
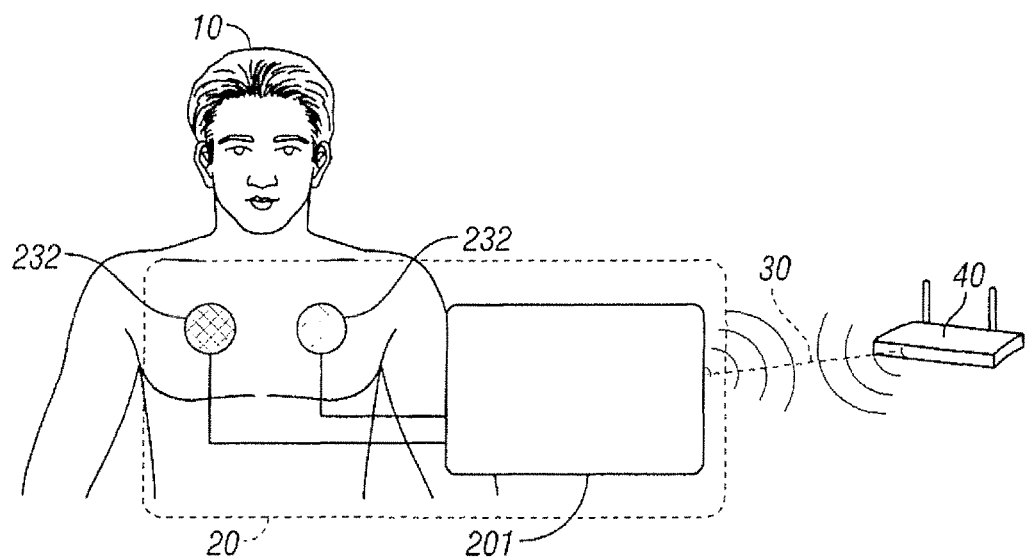
FIG. 4 is a diagram illustrating a store-and-forward system implemented for the vital-signs patch according to certain aspects of the subject disclosure.
Figure 5:
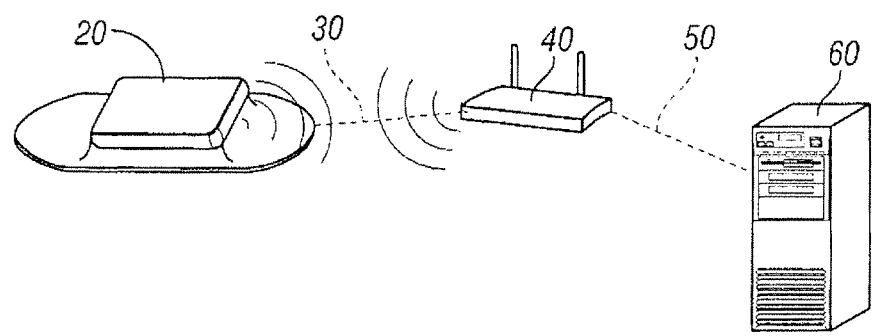
FIG. 5 is a diagram illustrating a store-and-forward system implemented for the bridge according to certain aspects of the subject disclosure.

FIG. 4 graphically illustrates a "store-and-forward" data transfer of vital sign measurements taken by the vital-sign patch 20 from, in this example, electrodes 232 by module 201 of patch 20 and forwarded from patch 20 to bridge 40. Some existing wireless devices that monitor vital signs such as cardiac pulse broadcast each measurement at the time the measurement was taken without confirmation that the data was received intact. In the embodiment described in FIG. 4, measurements are taken at regular intervals at the patient 10 while the vital sign signal transfer from patch 20 to bridge 40 over communication link 30 is at irregular intervals which are controlled by bridge 40 and which are not synchronized with the measurement intervals. Similarly, FIG. 5 graphically illustrates the "store-and-forward" transfer of vital sign signals received by bridge 40 from patch 20 over communication link 30 and then forwarded to server 60 over network link 50. There is no requirement that the transfer of data from bridge 40 to server 60 over network link 50 be synchronized with the transfer of data from patch 20 over communication link 30 to bridge 40.

Figure 6:
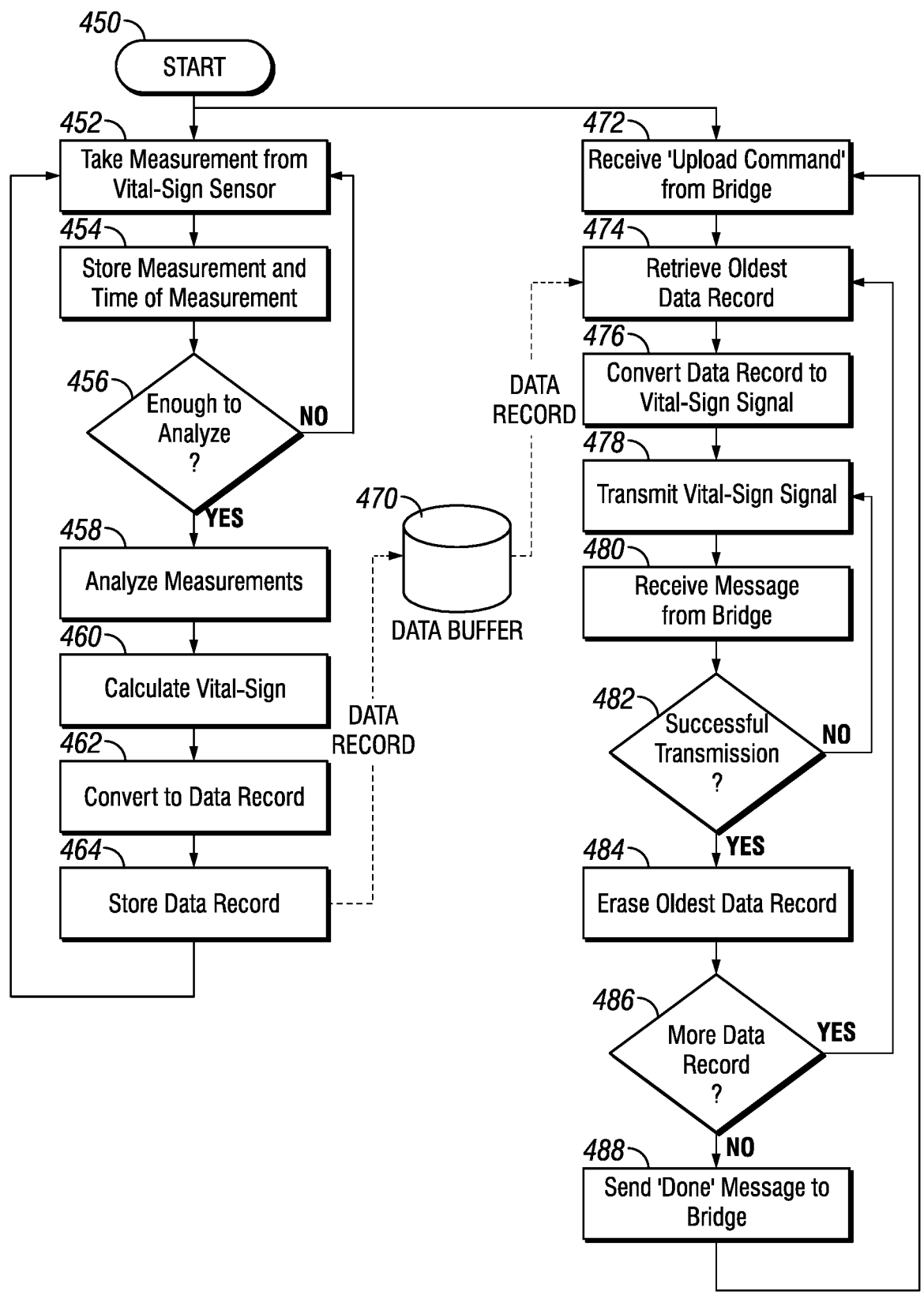
FIG. 6 is a flowchart showing a store-and-forward methodology implemented for the vital-signs patch according to certain aspects of the subject disclosure.

FIG. 6 is a flowchart that illustrates an exemplary store-and-forward methodology as implemented for the vital-signs patch according to certain embodiments of the present disclosure. As will be apparent to one of ordinary skill in the art, there are numerous variations of the principles disclosed in this specific example and in the examples that follow. Steps may be performed in a different order, some steps omitted, other steps added, and the logic flow may be varied without departing from the scope of the subject disclosure.

The process of FIG. 6 starts at step 450 when patch 20 is applied to a patient and activated. In this example, the sensor will be a pair of electrodes 28 (FIG. 2B) and the vital sign of interest is respiration, although patch 20 may have other sensors and may be measuring other vital signs instead of or in addition to respiration. Processor 202 of patch 20 takes a voltage measurement from the electrodes in step 452 and the measurement and the time at which the measurement was taken are stored in memory 202 in step 454. As determining the rate of respiration requires a series of measurements that are evaluated as a set, step 456 branches back to step 452 at this point. After a sufficient number of measurements are recorded, step 456 will branch to step 458 where the data is analyzed, in this example to find two successive peaks in the measurements, and the respiration rate is calculated, in this example, from the time interval between these peaks, in step 460. This calculated value is converted to a data record in step 462, in this example, by storing a record sequence number, the time of the second peak value, and the calculated respiration rate in a defined data structure, and in step 464 the data record is stored in data buffer 470 located, in this example, in memory 202.

In parallel with the process of steps 452 through 464, a second process of steps 472 through 488 is being independently executed. Patch 20 is listening with receiver 206 for a signal from bridge 40. Upon receipt in step 472 of an 'upload' command from bridge 40, this second process is initiated. Patch processor 20 will retrieve the oldest data record, as indicated in this example by the sequence number assigned in the first process, from data buffer 470 in step 474. The data record is converted in step 476 to a vital-sign signal according to the communication protocol of link 30 and transmitted to bridge 40 in step 480. Patch 20 then waits for a signal from bridge 40 as to whether the transmission was successful. If the message from the bridge is that the transmission was not correctly received, step 482 will branch back to step 478 and resend the same vital-sign signal. If the message from the bridge is that the transmission was successful, step 482 will bridge to step 484 where the data record associated with the transmission, which is the oldest record in data buffer 470, is erased. If more data records are available to transmit, step 486 branches back to step 474 to process the next-oldest record. If there are no more records ready to transmit, patch 20 sends a 'done" message to bridge 40 and returns to step 472 to await the next 'upload' command.

A patch 20 may lose communication with bridge 40, for example, when a patient travels to a part of the hospital where there are no bridges 40. If a patch 20 is out of communication with any bridge 40 for a period of time exceeding the measurement interval of step 452, then patch 20 will continue to make and store vital sign measurements following the loop 452-456-464-452. In some embodiments, patch 20 may comprise enough memory to hold several hours of vital sign measurements.

It can be seen that there is potential for a delay between the completion of a measurement by patch 20 of the vitals signs of a patient 10 and the successful transmission of the data from this measurement to bridge 40. This delay may be due to the periodic nature of communication between patch 20 and bridge 40 as designed into the protocol of communication link 30 or by travel by patient 10 out of the range of bridge 40.

Figure 7:
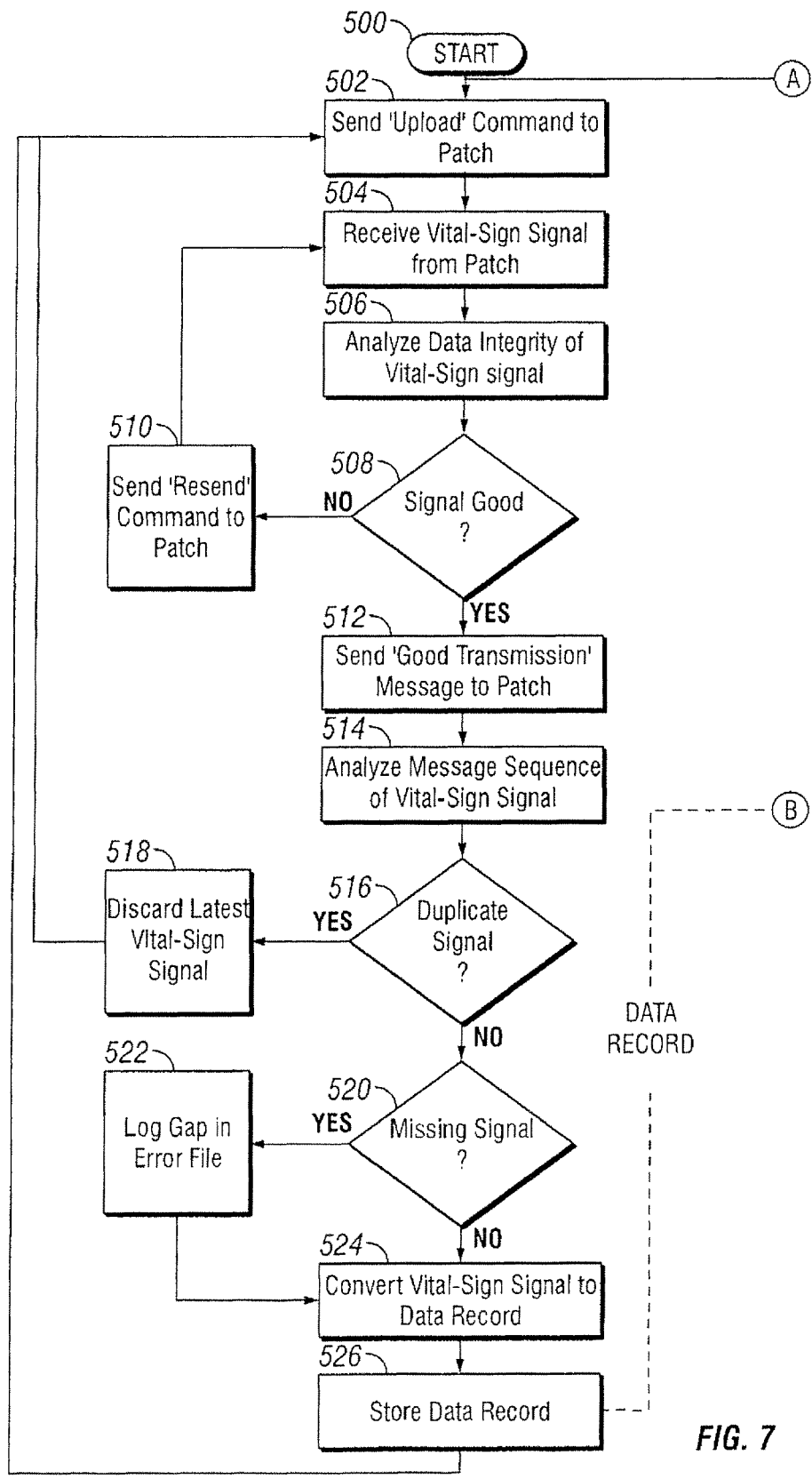
FIG. 7 is a flowchart showing a store-and-forward methodology implemented for the bridge according to certain aspects of the subject disclosure.
Figure 7:
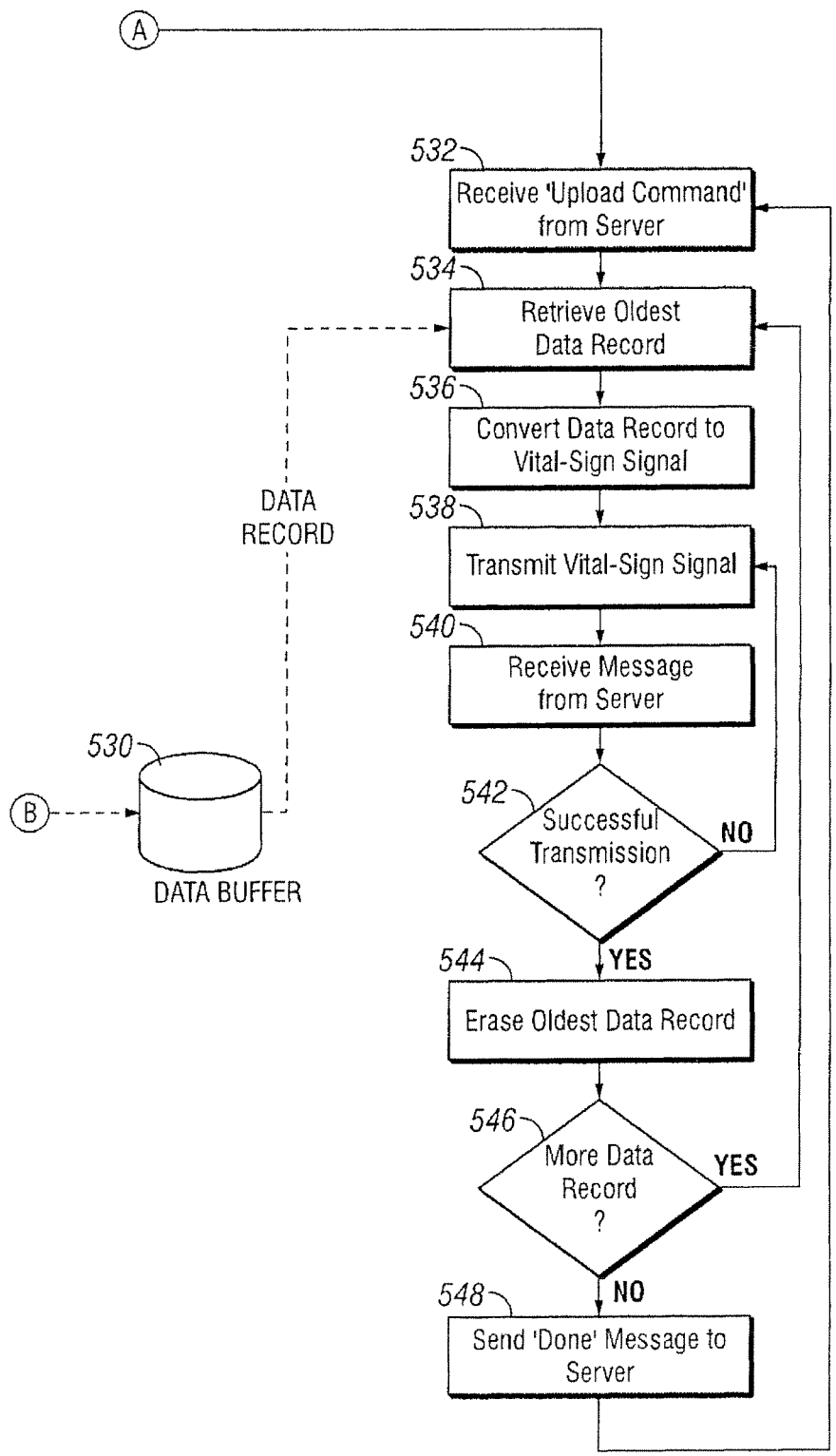

FIG. 7 is a flowchart that illustrates an embodiment of the store-and-forward methodology as implemented for the bridge. As will be apparent to one of ordinary skill in the art, there are numerous variations of the principles disclosed in this specific example. Steps may be performed in a different order, some steps omitted, other steps added, and the logic flow may be varied without departing from the scope of the subject disclosure.

In this example, the process starts at step 500 and proceeds to step 502 where bridge 40 sends an 'upload' command to patch 20. Bridge 40 then receives a vital-sign signal from patch 20 in step 504. In this example, the vital-sign signal is structured as a data packet that includes a packet identification value and a data integrity value.

The packet identification value may be unique over some duration of activity such that the system can determine whether a received data packet is a duplicate of a packet previously received (i.e. two packets have the same packet identification value) or whether a data packet has been missed (i.e. there is a gap in the sequence of packet identification values). For example, the packet identification value may be a numeric string composed of the serial number of patch 20 followed by a sequence number where the sequence number is, in this example, incremented by one for each new packet that is sent. If a packet is retransmitted, the same sequence number is used as was used for the initial transmission.

The data integrity value may be a Cyclic Redundancy Check (CRC) value or other error-detection value that is used to verify that the packet has been received without corruption at an acceptable level of certainty. Use of a CRC value to verify the integrity of a data signal is well known in the art. As a data integrity check of this type may not provide 100% certainty that an error in transmission has not occurred, other types of error-detection algorithms may be used to provide a higher degree of assurance that the signal has not been corrupted in transit.

In step 506, bridge 40 analyzes the data integrity of the vital-sign signal data packet using the CRC value. If an error in the data packet is detected, step 508 branches to step 510 where bridge 40 sends a 'resend' command to patch 20 and the process reverts to step 504. If no error is detected in the vital-sign signal, step 508 branches to step 512 where bridge 40 sends a "good transmission" signal to patch 20 and proceeds to step 514 where the message sequence is evaluated. If the sequence number indicates that this vital-sign signal is a duplicate of a previous successfully-received signal, step 516 branches to step 518 where this signal is discarded and the process reverts to step 502. If the sequence number indicates that a vital-sign signal was lost, in this example by a gap between the message sequence number of this vital-sign signal and the message sequence number of the last signal, step 520 branches to step 522 which logs the gap. Regardless of a gap, the process then reaches step 524 where the vital-sign signal is converted to a data record and stored in step 526 in data buffer 530.

In parallel with the process of steps 502 through 526, a second process of steps 532 through 548 is being independently executed. In step 532, bridge 40 is listening for an upload command from server 60. This step may be implemented in a number of configurations according to the protocol of network link 50, some of which include actions by the bridge to determine whether it is appropriate to initiate a transmission, without departing from the scope of the subject disclosure. Upon determination that it is appropriate to send data to the server, the process moves to step 534 where the oldest data record is retrieved from data buffer 530. The data record is converted to a vital-signs signal according to the protocol of network link 50 in step 536 and transmitted to server 60 in step 538. Bridge 40 then waits for a signal from the server in step 540 as to whether the transmission was successfully received. If the transmission was not successfully received, step 542 branches back to step 538 and resends the same signal. If the signal was successfully received, step 542 branches to step 544 and erases the oldest data record, which was associated with the signal just sent. If there are more data records available to transmit, step 546 branches to step 534 and retrieves the next-oldest record. If there are no more records ready to transmit, step 546 branches to step 548 and sends a 'done' message to the server, according to the protocol of network link 50, and returns to step 532 to await initiation of the next upload sequence.

Figure 8A:
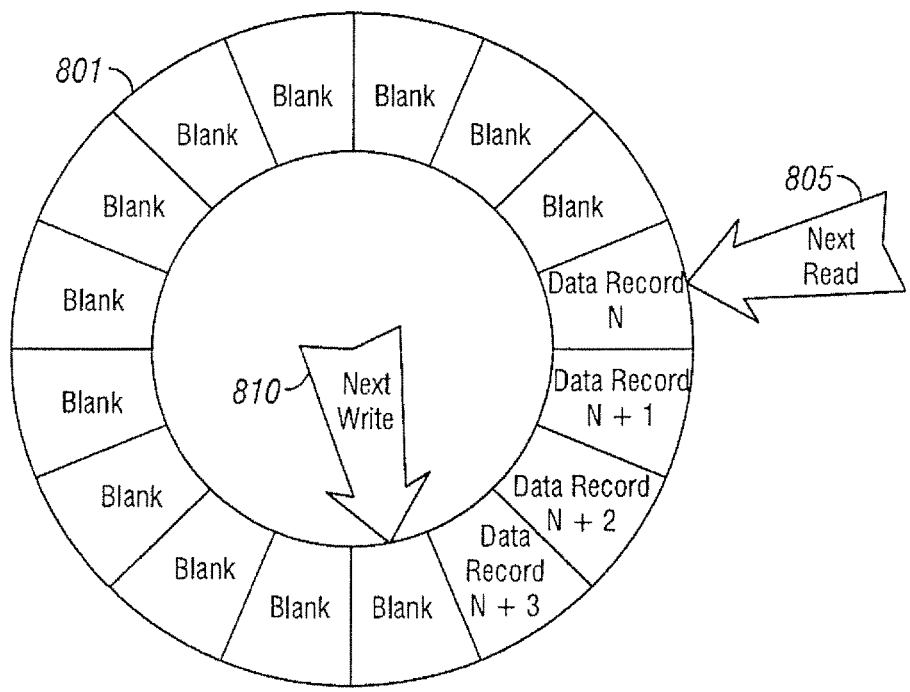
FIGS. 8A and 8B are diagrams that illustrate the function of a circular data buffer according to certain aspects of the subject disclosure.
Figure 8B:
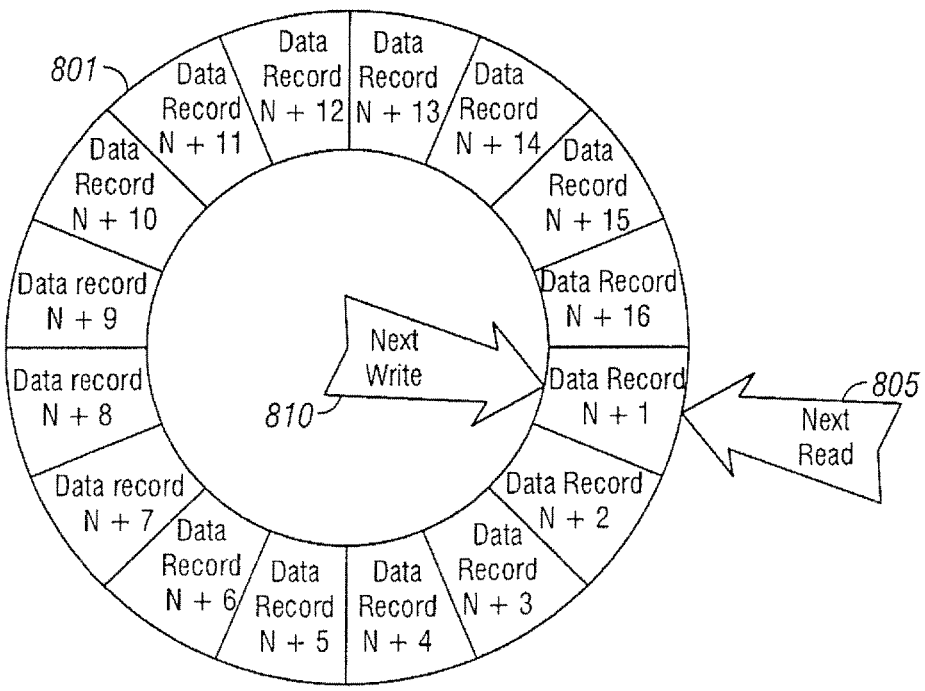

FIGS. 8A and 8B illustrate the configuration and use of a circular data buffer 801 in certain embodiments of the present disclosure. In this example, data buffer SOL located in memory 202, is able to store 16 data records but a data buffer may be of any size, limited only by the available storage capacity of the device. Circular data buffers are especially advantageous where the storage capacity is limited, such as in an embedded microprocessor system. The depiction of data buffer 801 as a circle of storage locations is intended to assist in understanding, as the designation of the storage locations has no physical significance.

In FIG. 8A, data records are stored in sequential locations in data buffer 801 and each data record has a number associated with the sequence in which the records were stored. In this example, the oldest data record is number "N" and the latest record is "N+3". Two pointers are associated with data buffer 801. The 'next write' pointer 810 indicates which storage location of data buffer 801 will be used for the next data record to be received. The 'next read' pointer 805 indicates the storage location of data buffer 801 that contains the oldest data record that is the data record that will be transmitted first. The number of records from the 'next read' pointer 805 to the 'next write' pointer 810 indicates the amount of data currently stored in data buffer 801. In this example, there are 4 records in data buffer 801, which has a capacity of 16, so the buffer is 25% full.

In normal operation, storage of new data records and reading of old data records happen independently. New data records may be received asynchronously from data records being read. For example, a new data record may be received at a fixed time interval while data records may be read in groups at irregular intervals. During times when more new data records are received than old data records are read, data buffer 801 will become increasingly full. During times when more data records are read than new data records are received, data buffer 801 will become increasingly empty until there are no data records stored in data buffer 801. It is desirable to select the size of data buffer 801 to be large enough to store the largest number of data records that might accumulate.

In FIG. 8B, circular data buffer 801 is full. This may occur when there is an interruption in the reading of data records for a period of time longer than anticipated by the software programmer. In this example, the oldest existing data record is "N+1" and the last record stored is "N+16". After record "N+16" was received and stored, the 'next read' pointer 810 and 'next write' pointer 805 both indicate the same record. When the next record is received, it would be stored in the same location as currently occupied by record "N+1", erasing record "N+1" resulting in loss of the data in data record "N+1". This is termed "circular buffer overflow."

Figure 9A:
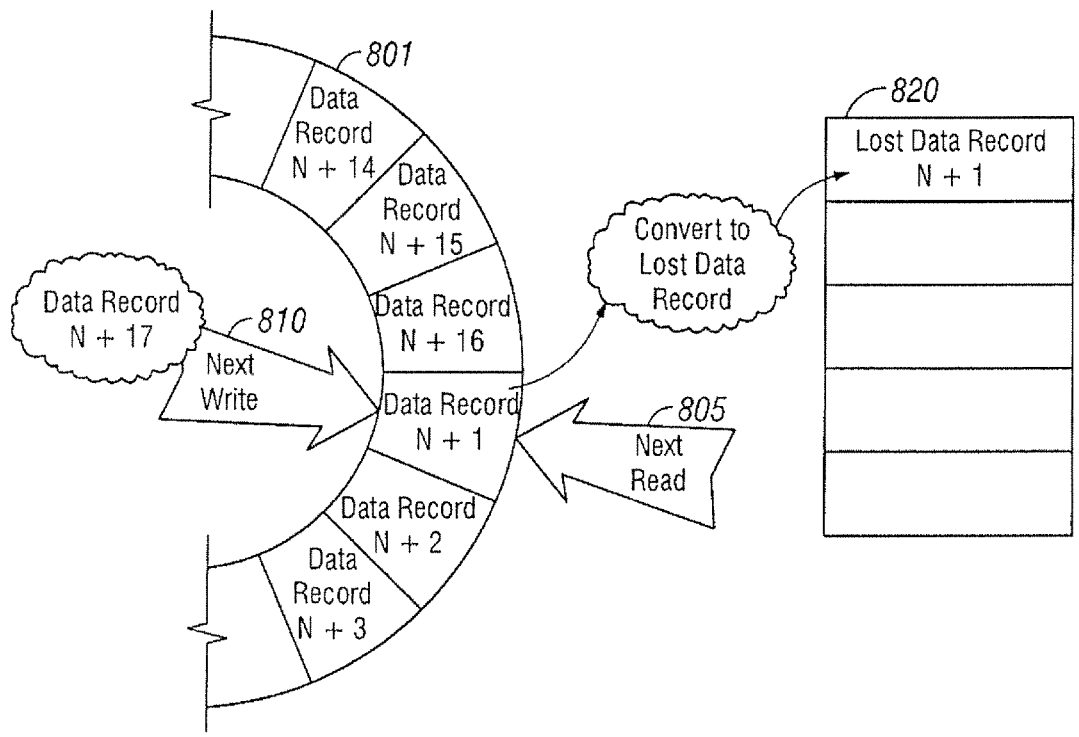
FIGS. 9A and 9B are diagrams that illustrate a process for managing circular buffer overflow using lost data records according to certain aspects of the subject disclosure.
Figure 9B:
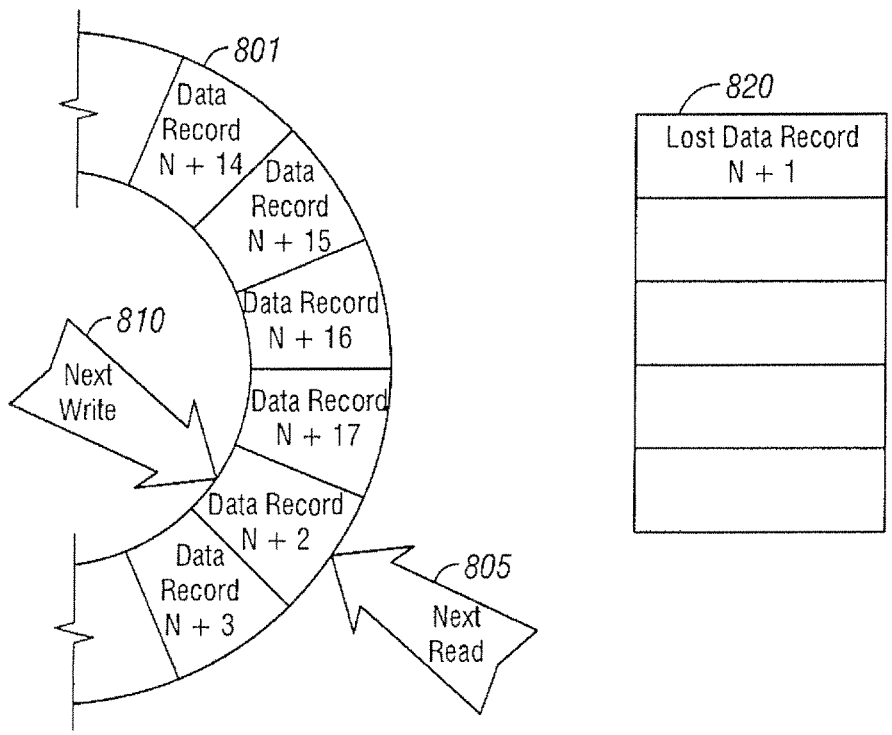

FIGS. 9A and 9B describe an exemplary embodiment of a method of handling circular buffer overflow according to certain embodiments of the present disclosure. In FIG. 9A, data record "N+17" has been received but is not yet written into data buffer 801. The processor first reads data record "N+1" and extracts key information such as the time of the reading and whether the reading is within limits. This key information is stored as a "lost data record" in array 820 which occupies a separate area of memory 202. The lost data record is much smaller than the data record from which it is created, possibly as small as a single bit depending on how much information the programmer wishes to retain. Once lost data record "N+1" is created, the 'next read' pointer 805 is reset to indicate data record "N+2" and then data record "N+17" is written into the buffer location occupied by data record "N+1". FIG. 9B illustrates the configuration of the buffer at the end of the storage operation, with the oldest record in the buffer now being data record "N+2" and the newest record being data record "N+17", both the 'next write' pointer 810 and 'next read' pointer 805 indicating the buffer location occupied by data record "N+2", and with a separate lost data record "N+1" stored in the first location of array 820.

Alternate forms of a lost data record may be a single register that stores the number of data records that have been overwritten, or a pair of registers that store the number of overwritten records that were within limits and that exceeded limits. The advantage of these alternate methods is that they occupy a very small and fixed amount of memory while being able to handle a relatively large number of lost data records, up to the allocated size of the registers. The disadvantage is that the amount of information retained regarding the values of the lost data records is very small.

It can be seen that the disclosed embodiments of the vital-signs monitor patch provide a mobile solution to monitoring the vital signs of a patient. The design of the vital-signs monitor patch frees nurses, or other caregivers, from the task of repetitively measuring the vital signs of their patients, allowing the caregivers to spend more time on other duties. The ability to continuously monitor a patient's vital signs using a monitor patch, together with the rest of the patient monitoring system, increases the ability of the nurse to respond quickly to a sudden change in a patient's condition, resulting in improved care for the patient.

The store-and-forward capability of the patch enables the patch to accumulate vital-sign measurements while the patient is out of range of a bridge and, up to certain interval of time out of communication, transfer this data to the rest of the patient monitoring system without loss of data taken during the time out of communication. Furthermore, in cases where the patient is out of range of a bridge for a period of time exceeding the storage limits of the patch, a reduced amount of information related to the oldest measurements is retained and, when the patch regains a communication link to the rest of the patient monitoring system, information is sent to the system regarding the lost measurements in addition to the complete records of the latest measurements. Furthermore, because the data is stored, the data can be retained by the patch until the bridge confirms that the data was received intact and if a data transfer was corrupted, the same data can be resent. This retention of data until receipt is confirmed increases the reliability of the communication link between the patch and bridge.

The store-and-forward capability of the bridge enables the bridge to receive data from each patch to which the bridge is assigned at times determined by the bridge. The time at which this same information is transferred from the bridge to the server can be selected by the server to optimize other characteristics of the system, such as load management of the server-to-bridge communication link. This decoupling of the timing of the patch-to-bridge data transfer from the bridge-to-server data transfer increases the reliability of the end-to-end linkage from a patch to the server as the transfer over each link can be verified without impact to the next link of the transfer chain.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vital-signs patch for a patient monitoring system, the patch comprising:
   a patch housing configured for wearing by a patient, the patch housing containing:
      at least one sensor configured to obtain physiological measurements related to a vital-sign of a patient;
      a transmitter configured to transmit signals to a remote device;
      a receiver configured to receive signals from the remote device;
      a memory configured to store executable instructions and data records; and
      a processor operably connected to the sensor, the transmitter, the receiver, and the memory, and configured to execute the instructions;
   wherein the processor is configured to periodically obtain, from the at least one sensor, the physiological measurements, process the physiological measurements, and, after a predetermined number of physiological measurements are obtained from the sensor, determine two successive peaks in the physiological measurements and a time of an occurrence of each peak of the two successive peaks, determine a rate of the physiological measurements based on a time interval between a first peak and a second peak of the determined two successive peaks, and convert the physiological measurements, a time of the first peak, a time of the second peak and, the determined rate of the physiological measurements to data records by storing, in the memory, the physiological measurements, the time of the first peak, the time of the second peak and the determined rate in a defined data structure; and
   wherein the processor is further configured to receive one or more signals associated with an upload command from the remote device via the receiver and, in response to the receipt of the one or more signals:
      retrieve at least a portion of the data records from the memory, and
      cause the transmitter to transmit the retrieved portion of the data records to the remote device.

2. The vital-signs patch of claim 1, wherein the physiological measurements of the patient include measurements of vital-signs comprising at least one of body temperature, cardiac puke rate, respiration rate, and blood pressure.

3. The vital-signs patch of claim 2, wherein the sensor comprises one or more electrodes.

4. The vital-signs patch of claim 1, wherein the data records are structured as a data packet, wherein the data packet comprises a data packet identification value and a data integrity value.

5. The vital-signs patch of claim 1, wherein the processor is configured to store the data records as successive data records.

6. The vital-signs patch of claim 5, wherein the processor is configured to retain each data record in the memory until a signal indicating a successful transmission of the retrieved portion of the data records k received from the remote device, whereupon the processor is configured to erase the data records.

7. The vital-signs patch of claim 5, wherein the processor is further configured to store a predetermined number of the data records in sequential locations in a circular buffer within the memory.

8. The vital-signs patch of claim 7, wherein the processor, when the circular buffer becomes full, is further configured to create a lost-data record that comprises information regarding the last recently stored data record, store the lost-data record in an array separate from the circular buffer, and then overwrite the last recently stored data record with a new data record.

9. A vital-signs patch for a patient monitoring system, the patch comprising:
a patch housing configured for wearing by a patient, the patch housing containing:
at least one sensor configured to obtain physiological measurements of a vital of a patient;
a transmitter configured to transmit signals to a remote device;
a receiver configured to receive signals from the remote device;
a memory configured to store executable instructions and data records; and
a processor operably connected to the sensor, the transmitter, the receiver, and the memory, and configured to execute the instructions;
wherein the processor is configured to periodically obtain, from the at least one sensor, the physiological measurements, process the physiological measurements, and, after a predetermined number of physiological measurements are obtained from the sensor, determine two successive peaks in the physiological measurements and a time of an occurrence of each peak of the two successive peaks, determine a rate of the physiological measurements based on a time interval between a first peak and a second peak of the determined two successive peaks, and convert the physiological measurements, a time of the first peak, a time of the second peak and, the determined rate of the physiological measurements to data records by storing, in the memory, the physiological measurements, the time of the first peak, the time of the second peak and the determined rate in a defined data structure;
wherein the processor is further configured to receive one or more signals associated with an upload command from the remote device via the receiver and, in response to the receipt of the one or more signals:
retrieve at least a portion of the data records from the memory, and
cause the transmitter to transmit the retrieved portion of the data records to the remote device; and
wherein the retrieved portion of data records is received at the remote device as a structured data packet, wherein the data packet comprises a data packet identification value and a data integrity value, and wherein the processor is further configured to use the data packet identification value to verify that the data packet is not a duplicate of a previously received data packet.

10. The vital-signs patch of claim 9, wherein the physiological measurements of the patient include measurements of vital-signs comprising at least one of body temperature, cardiac puke rate, respiration rate, and hood pressure.

11. The vital-signs patch of claim 10, wherein the sensor comprises one or more electrodes.

12. The vital-signs patch of claim 9, wherein the processor is configured to store the data records from the physiological measurements as successive data records.

13. The vital-signs patch of claim 12, wherein the processor is configured to retain each data record in the memory until a signal indicating a successful transmission of the retrieved portion of the data records is received from the remote device, whereupon the processor is configured to erase the data records.

14. The vital-signs patch of claim 12, wherein the processor is configured to store a predetermined number of the data records in sequential location in a circular buffer within the memory.

15. The vital-signs patch of claim 14, wherein the processor, when the circular buffer becomes full, is further configured to create a lost-data record that comprises information regarding the last recently stored data record, store the lost-data record in an array separate from the circular buffer, and then overwrite the last recently stored data record with a new data record.

16. A vital-signs patch for a patient monitoring system, the patch comprising:
a patch housing configured for wearing by a patient, the patch housing containing:
at least one sensor configure to obtain physiological measurements of a patient;
a transmitter configured to transmit signals to a remote device;
a receiver configured to receive signals from the remote device;
a memory configured to store executable instructions and data records; and
a processor operably connected to the sensor, the transmitter, the receiver, and the memory, and configured to execute the instructions;
wherein the processor is configured to periodically obtain, from the at least one sensor the physiological measurements, process the physiological measurements, and, after a predetermined number of physiological measurements are obtained from the sensor, determine two successive peaks in the physiological measurements and a time of an occurrence of each peak of the two successive peaks, determine a rate of the physiological measurements based on a time interval between a first peak and a second peak of the determined two successive peaks, and convert the physiological measurements, a time of the first peak, a time of the second peak and, the determined rate of the physiological measurements to data records by storing, in the memory, the physiological measurements, the time of the first peak, the time of the second peak and the determined rate in a defined data structure;
wherein the processor is configured to store the data records;
wherein the processor is configured to retain each data record of the data records in memory until a signal indicating a successful transmission of a data record is received from the remote device, whereupon the processor is configured to erase the data record; and
wherein the processor is further configured to receive one or more signals associated with an upload command from the remote device via the receiver and, in response to the receipt of the one or more signals:
retrieve at least a portion of the data records, and
cause the transmitter to transmit the retrieved portion of the data records to the remote device.

17. The vital-signs patch of claim 16, wherein the data records are structured as a data packet, wherein the data packet comprises a data packet identification value and a data integrity value.

18. The vital-signs patch of claim 16, wherein the processor is further configured to store a predetermined number of the data records in sequential locations in a circular buffer within the memory.

19. The vital-signs patch of claim 18 wherein the processor, when the circular buffer becomes full, is further configured to create a lost-data record that comprises information regarding the last recently stored data record, store the lost-data record in an array separate from the circular buffer, and then overwrite the last recently stored data record with a new data record.

20. A sensor patch, comprising:
   a sensor configured to obtain at least one physiological measurement;
   a receiver and a transmitter;
   a processor configured to obtain the at least one physiological measurement, wherein the at least one physiological measurement includes a respiration measurement; and
   a memory,
   wherein the processor is configured to:
      periodically obtain, from the sensor, a plurality of physiological measurements and a time the plurality of physiological measurements were obtained by the sensor;
      record, in the memory, the plurality of physiological measurements together with a plurality of times at which each of the plurality of physiological measurements are obtained;
      after a predetermined number of the plurality of physiological measurements are recorded, determine two successive peaks in the recorded plurality of physiological measurements;
      determine a rate of respiration based on a time interval between a first peak and a second peak of the determined two successive peaks;
      store, in the memory, a record including the physiological measurements, a time of the first peak, a time of the second peak and, the determined rate of respiration in a defined data structure;
      listen, using the receiver, for an upload command from a remote bridge device; and
   upon receiving the upload command, retrieve the record and send the record, using the transmitter, to the remote bridge device,
      wherein the sensor, the receiver and the transmitter, the processor and the memory are substantially enclosed in a housing configured to be applied to a living body.

* * * * *